US005792760A

United States Patent [19]
Hipskind et al.

[11] Patent Number: 5,792,760
[45] Date of Patent: Aug. 11, 1998

[54] BISINDOLES AS TACHYKININ RECEPTOR ANTAGONISTS

[75] Inventors: Philip A. Hipskind, New Palestine; Karen L. Lobb, Indianapolis, both of Ind.

[73] Assignee: Eli Lilly and Company, Indianapolis, Ind.

[21] Appl. No.: 838,960

[22] Filed: Apr. 23, 1997

[51] Int. Cl.⁶ .................. C07D 401/14; C07D 403/14; A61K 31/445; A61K 31/405
[52] U.S. Cl. .................. 514/212; 514/323; 514/414; 540/602; 546/201; 548/455
[58] Field of Search .................. 546/201; 514/323, 514/212, 414; 540/602; 548/455

[56] References Cited

U.S. PATENT DOCUMENTS 5,565,568  10/1996  Cho et al. .................. 544/373

FOREIGN PATENT DOCUMENTS 9738692  10/1997  WIPO .

Primary Examiner—Mukund J. Shah
Assistant Examiner—Ann M. Kessinger
Attorney, Agent, or Firm—Paul J. Gaylo; David E. Boone

[57] ABSTRACT

This invention provides a series of substituted bisindole propanamides which are useful as tachykinin receptor antagonists and as serotonin agonists. This invention also provides methods for the treatment of related disorders as well as pharmaceutical formulations which employ these novel compounds.

2 Claims, No Drawings

5,792,760

1

BISINDOLES AS TACHYKININ RECEPTOR ANTAGONISTS

BACKGROUND OF THE INVENTION

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1:41 (1978); H. W. M. Steinbusch, HANDBOOK OF CHEMICAL NEUROANATOMY, Volume 3, Part II, 68 (1984); N. E. Anden, et al., Acta *Physiologica Scandinavia*, 67:313 (1966). These studies have been complemented by biochemical evidence that indicates large concentrations of 5-HT exist in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, BIOLOGY OF SEROTONERGIC TRANSMISSION, 221 (1982); D. J. Boullin, SEROTONIN IN MENTAL ABNORMALITIES 1:316 (1978); J. Barchas, et al., *Serotonin and Behavior*,(1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Serotonin may be taken up by the platelets and, upon platelet aggregation, be released such that the cardiovascular system provides another example of a peripheral network that is very sensitive to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophrenia, autism, neurodegenerative disorders, such as Alzheimer's disease, Parkinsonism, and Huntington's chorea, and cancer chemotherapy-induced vomiting. M. D. Gershon, et al., THE PERIPHERAL ACTIONS OF 5-HYDROXYTRYPTAMINE, 246 (1989); P. R. Saxena, et al., *Journal of Cardiovascular Pharmacology*, 15: Supplement 7 (1990).

Serotonin produces its effects on cellular physiology by binding to specialized receptors on the cell surface. It is now recognized that multiple types of receptors exist for many neurotransmitters and hormones, including serotonin. The existence of multiple, structurally distinct serotonin receptors has provided the possibility that subtype-selective pharmacological agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of 5-HT$_1$-like receptors on the endothelial cells produces vasodilation while stimulation of 5-HT$_2$ receptors on the smooth muscle cells produces vasoconstriction.

Currently, the major classes of serotonin receptors (5-HT$_1$, 5-HT$_2$, 5-HT$_3$, 5-HT$_4$, 5-HT$_5$, 5-HT$_6$, and 5-HT$_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14:35 (1990).]

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see, e.g., S. L. Shepheard, et al., *British Journal of Pharmacology*, 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,491,140, issued Feb. 13, 1996; U.S. Pat. No. 5,328,927, issued Jul. 12, 1994; U.S. Pat. No. 5,360,820, issued Nov. 1, 1994; U.S. Pat. No. 5,344,830, issued Sept. 6, 1994; U.S. Pat. No. 5,331,089, issued Jul. 19, 1994; European Patent Publication 591,040

A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993; Canadian Patent Application 2154116, published Jan. 23, 1996; European Patent Publication 693,489, published Jan. 24, 1996; and Canadian Patent Application 2151116, published Dec. 11, 1995.

U.S. patent application Ser. No. 08/318,391, filed Oct. 5, 1994, describes a synergistic effect on the combination of a serotonin agonist and a tachykinin receptor antagonist in treating migraine. U.S. patent application Ser. No. 08/387, 056, filed Feb. 10, 1995, describes a synergistic effect on the combination of a serotonin agonist and a tachykinin receptor antagonist in treating a variety of psychiatric disorders. U.S. patent application Ser. No. 08/408,238, filed Mar. 22, 1995, describes a synergistic effect on the combination of a serotonin agonist and a tachykinin receptor antagonist in treating a variety of types of pain and nociception. U.S. patent application Ser. No. 60/000,074, filed Jun. 8, 1995, describes a synergistic effect on the combination of a serotonin agonist and a tachykinin receptor antagonist in treating the common cold or allergic rhinitis.

Because of the current dissatisfaction of the currently marketed treatments for treating the above-described indications within the affected population, there exists a need for a more efficacious and safe treatment.

SUMMARY OF THE INVENTION

This invention provides the compounds of Formula I

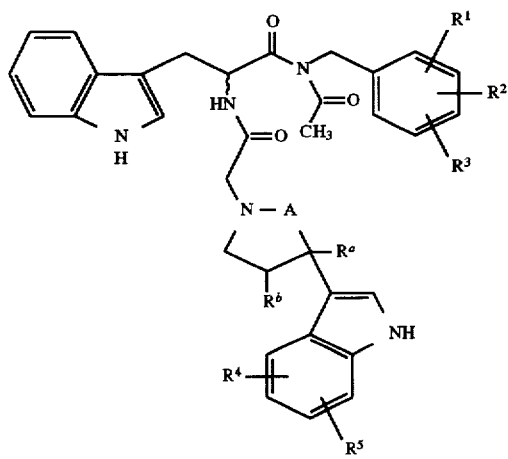

wherein:
- $R^1$, $R^2$, and $R^3$ are independently hydrogen, halo, $C_1$-$C_6$ alkoxy, $C_1$-$C_6$ alkylthio, nitro, trifluoromethyl, or $C_1$-$C_6$ alkyl;
- A is —$CH_2$—, —$CH_2CH_2$—, or —$CH_2CH_2CH2$—;
- $R^a$ is hydrogen or hydroxy, and $R^b$ is hydrogen, or $R^a$ and $R^b$ are taken together to form a bond;
- $R^4$ and $R^5$ are independently taken from the group consisting of halo, trifluoromethyl, hydrogen, $C_1$-$C_6$ alkoxy, $C_1$-$C_6$ alkyl, $C_1$-$C_6$ alkylthio, $C_1$-$C_6$ alkylamino, hydroxy, cyano, $C_2$-$C_7$ alkanoyl, $C_2$-$C_7$ alkanoyloxy, benzamido, phenoxy, carboxamido, hydroxy, benzyloxy, phenyl($C_2$-$C_7$ alkanoyl)-, $C_1$-$C_6$ phenyl($C_2$-$C_7$ carbamoyl)-,
- said benzamido, phenoxy, benzyloxy, phenyl($C_2$-$C_7$ alkanoyl)-, and phenyl($C_2$-$C_7$ carbamoyl)-being optionally substituted with one or more groups selected from the group consisting of halo, trifluoromethyl, $C_1$-$C_6$ alkyl, $C_1$-$C_6$ alkoxy, cyano, hydroxy, amino and nitro;

or a pharmaceutically acceptable salt or solvate thereof.

This invention also provides methods of treating conditions associated with an excess of tachykinins, which comprises administering to a mammal in need thereof an effective amount of a compound of Formula I.

The present invention, in another embodiment, provides methods of treating conditions associated with an inappropriate stimulation of a serotonin receptor, which comprises administering to a mammal in need thereof, a compound of Formula I.

This invention also provides methods for treating or preventing a number of disorders characterized by their being affected, in a synergistic manner, by a combination of a serotonin agonist and a tachykinin receptor antagonist, which comprise administering to a mammal in need thereof an effective amount of a compound of Formula I or a pharmaceutically acceptable salt or solvate thereof. Among these disorders are: pain or nociception; migraine; the common cold; allergic rhinitis; or a psychiatric disorder selected from the group consisting of panic disorder, panic attack, depression, anxiety, bulimia nervosa, obsessive-compulsive disorder, premenstrual dysphoric disorder, substance abuse, substance dependence, agoraphobia, post-traumatic stress disorder, dementia of Alzheimer's type, social phobia, attention deficit hyperactivity disorder, disruptive behavior disorder, intermittent explosive disorder, borderline personality disorder, chronic fatigue syndrome, premature ejaculation, and depression and behavioral problems associated with head injury, mental retardation, and stroke.

This invention also provides pharmaceutical formulations which comprise a compound of Formula I, or a pharmaceutically acceptable salt or solvate thereof, in combination with one or more pharmaceutically acceptable carriers, diluents, or excipients therefor.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "FDMS" refers to field desorption mass spectrometry;

"UV" refers to ultraviolet spectroscopy; "IR" refers to infrared spectroscopy; and "NMR" refers to nuclear magnetic resonance spectroscopy.

As used herein, the term "$C_1$-$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$-$C_6$ alkyl" includes within its definition the term "$C_1$-$C_4$ alkyl".

"Halo" represents chloro, fluoro, bromo or iodo.

"$C_1$-$C_6$ alkylthio" represents a straight or branched alkyl chain having from one to six carbon atoms attached to a sulfur atom. Typical $C_1$-$C_6$ alkylthio groups include methylthio, ethylthio, propylthio, isopropylthio, butylthio and the like. The term "$C_1$-$C_6$ alkylthio" includes within its definition the term "$C_1$-$C_4$ alkylthio".

"$C_1$-$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached through a carbonyl moiety. Typical $C_2$–$C_6$ alkanoyl groups include ethanoyl (also referred to as acetyl), propanoyl, isopropanoyl, butanoyl, t-butanoyl, pentanoyl, hexanoyl, and the like.

"$C_1$–$C_6$ alkylenyl" refers to a straight or branched, divalent, saturated aliphatic chain of one to six carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like.

The term "$C_2$–$C_7$ carbamoyl" as used herein refers to a moiety having one of the following two structures.

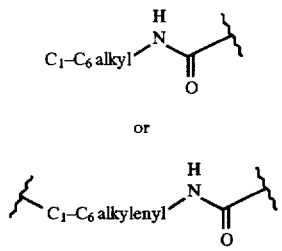

The term "heterocycle" represents a stable 5- to 7-membered monocyclic or 7- to 10-membered bicyclic heterocyclic ring which is saturated or unsaturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)- ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like;

benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, PROTECTIVE GROUPS IN ORGANIC CHEMISTRY, (J. G. W. McOmie, ed., 1973), at Chapter 2; and T. W. Greene and P. G. M. Wuts, PROTECTIVE GROUPS IN ORGANIC SYNTHESIS (1991), at Chapter 7.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The term "haloformate" as used herein refers to an ester of a haloformic acid, this compound having the formula

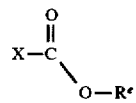

wherein X is halo, and $R^e$ is $C_1$–$C_6$ alkyl. Preferred haloformates are bromoformates and chloroformates. Especially preferred are chloroformates. Those haloformates wherein $R^3$ is $C_3$–$C_6$ alkyl are preferred. Most preferred is isobutyl chloroformate.

The compounds used in the method of the present invention may have one or more asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active acid or base. These diastereomers can then be separated using differential solubility, fractional crystallization, chromatography, or like methods. Further details regarding resolution of enantiomeric mixtures can be found in J. Jacques, et al., ENANTIOMERS, RACEMATES, AND RESOLUTIONS, (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention includes the pharmaceutically acceptable salts of the compounds defined by Formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further encompasses the pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, DESIGN OF PRODRUGS, (1985).

The preferred methods of the present invention employ the preferred compounds of the present invention. The preferred compounds of the present invention are those compounds of Formula I in which:

(1) at least one of $R^1$, $R^2$, and $R^3$ is not hydrogen;
(2) A is methylene or ethylene;
(3) $R^a$ and $R^b$ are both hydrogen, or $R^a$ and $R^b$ combine to form a bond; and
(4) at least one of $R^4$ and $R^5$ is chloro, fluoro, hydroxy, trifluoromethyl, methoxy, ethoxy, methyl, benzamido, and phenyl($C_2$–$C_7$ carbamoyl)-, or a substituted derivative thereof.

Especially preferred are those compounds of Formula I in which:

(1) A is methylene;
(2) $R^1$, $R^2$, and $R^3$, together with the phenyl group to which they are bound, form, 2-methoxyphenyl, 2-chlorophenyl, 2-methylphenyl, 2-trifluoromethylphenyl, 3,4-dimethoxyphenyl, 3,4-dichlorophenyl, 3,4-bis(trifluoromethyl)phenyl, 3,4,5-trimethoxyphenyl, 3,4,5-trichlorophenyl, 3,4,5-trimethylphenyl, 3,4,5-tri(trifluoromethyl)phenyl, 3,5-dimethoxyphenyl, 3,5-dichlorophenyl, 3,5-dimethylphenyl, or 3,5-bis(trifluoromethyl)phenyl;
(3) $R^a$ and $R^b$ are both hydrogen, or $R^a$ and $R^b$ combine to form a bond; and
(4) at least one of $R^4$ and $R^5$ is chloro, fluoro, hydroxy, trifluoromethyl, methoxy, ethoxy, methyl, benzamido, and phenyl($C_2$–$C_7$ carbamoyl)-, or a substituted derivative thereof, substituted at the five and/or six position of the indolyl moiety.

The compounds of the present invention may be prepared by reacting a compound of Formula II

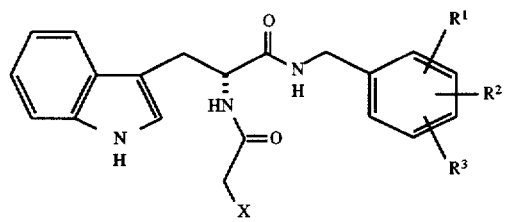

where X is a leaving group, preferably a halo group, most preferably bromo or iodo, with a compound of Formula III.

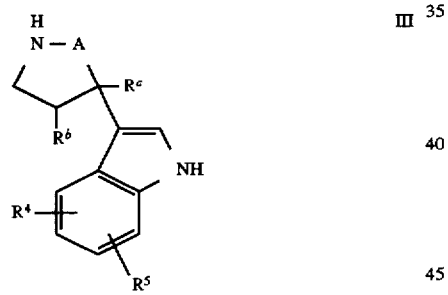

This reaction is generally performed in an organic solvent, at a temperature between −78° C. and 120° C., and the resulting product is isolated. This reaction is generally performed using equimolar amounts of the two reactants, even though other ratios may also be employed. The organic solvent used is preferably a polar aprotic solvent, for example, acetonitrile, N,N-dimethylformamide, N,N-dimethylphenylacetamide, dimethylsulfoxide, or hexamethylphosphoric triamide. Instead of using a polar aprotic solvent it is also possible to use an ether, such as tetrahydrofuran, dioxane, or methyl t-butyl ether, or a ketone, such as methyl ethyl ketone. Acetonitrile is the most preferred such solvent.

In the temperature range indicated above, the preferred temperature is 30°–90° C. If acetonitrile is employed as a solvent, the reaction is advantageously carried out at the reflux point of the reaction mixture.

The product obtained in this way is isolated by the usual techniques, for example, by concentration of the solvents, followed by washing of the residue with water, and then purification by conventional techniques, such as chromatography or recrystallization.

The compounds of the present invention may also be prepared by reacting a compound of Formula IV

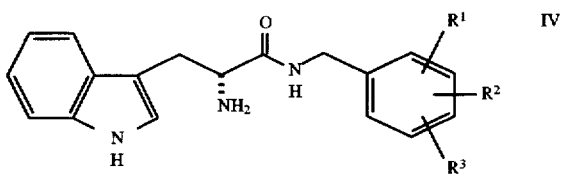

with a compound of Formula V

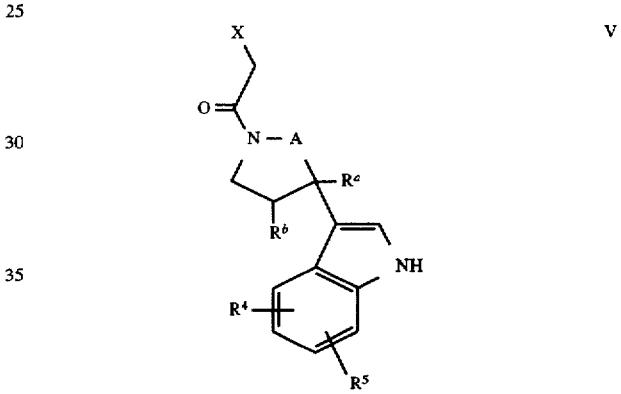

where X is a leaving group, preferably a halo group, most preferably bromo or iodo. The reaction conditions and the solvent employed for this reaction are essentially the same as for the reaction of the compounds of Formula II and III, supra.

The most preferred method of synthesizing the intermediates of Formulae II and IV is depicted in Scheme I, infra. Many of the steps of this synthesis are described in Patent Cooperation Treaty Publication WO 95/14017, published May 26, 1995, and European Patent Application Publication 693,489, published Jan. 24, 1996. The intermediates of Formula II are generally prepared as described in Patent Cooperation Treaty published application WO 93/01169, published Jan. 21, 1993. Once such synthesis scheme using standard techniques is depicted in Scheme I, infra.

Scheme I

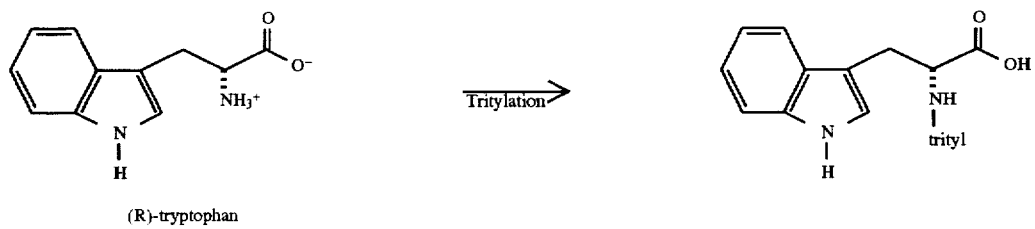

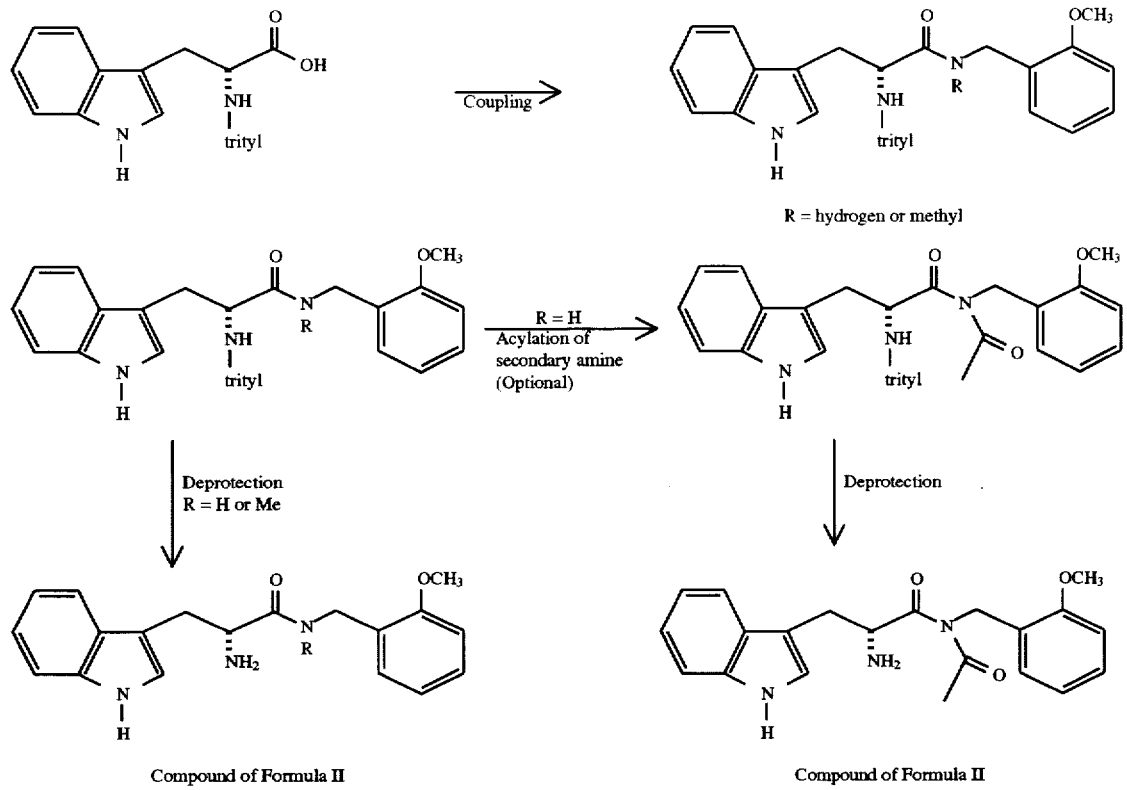

Compound of Formula II          Compound of Formula II

The coupling of the protected amine to the substituted benzylamine, as depicted in step (b), can be performed by many means known in the art, the particular methods employed being dependent upon the particular benzylamine which is used as the starting material and the type of protected amine used in the coupling reaction. These coupling reactions frequently employ commonly used coupling reagents such as 1, 1-carbonyl diimidazole, dicyclohexylcarbodiimide, diethyl azodicarboxylate, 1-hydroxybenzotriazole, alkyl chloroformate and triethylamine, phenyldichlorophosphate, and chlorosulfonyl isocyanate. Examples of these methods are described infra.

The acylation of the secondary amine can be done using any of a large number of techniques regularly employed by those skilled in organic chemistry. One such reaction scheme is a substitution using an anhydride such as acetic anhydride. Another reaction scheme often employed to acylate a secondary amine employs a carboxylic acid preferably with an activating agent. An amino-de-alkoxylation type of reaction uses esters as a means of acylating the amine. Activated esters which are attenuated to provide enhanced selectivity are very efficient acylating agents. One preferred such activated ester is p-nitrophenyl ester, such as p-nitrophenyl acetate.

The amine is then deprotected using standard techniques.

The particular deprotecting agents and conditions employed will depend upon the amino-protecting group utilized. For those compounds in which a trityl group is used to protect the amine, the use of dry gaseous hydrogen chloride in a suitable solvent, such as dry ethyl ether, is especially preferred.

The following Preparations and Examples further illustrate the compounds of the present invention and the methods for their synthesis. The Preparations and Examples are not intended to be limiting to the scope of the invention in any respect, and should not be so construed. All solvents and reagents were purchased from commercial sources and used as received, unless otherwise indicated. Dry tetrahydrofuran (THF) was obtained by distillation from sodium or sodium benzophenone ketyl prior to use.

The starting materials described herein are commercially available or may be prepared by methods well known to those in the art.

PREPARATION 1

Preparation of 2-t-butoxycarbonylamino-3-(1H-indol-3-yl)-N-(2-methoxybenzyl) propanamide

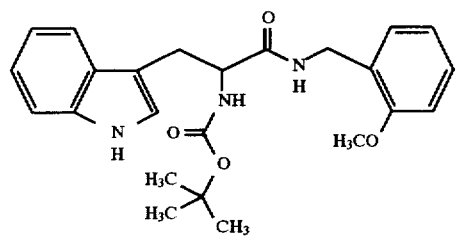

To a solution of N-(t-butoxycarbonyl)tryptophan (46.4 g, 152.6 mmol) in 500 ml of dioxane was added carbonyl diimidazole (25.4 g, 156 mmol) in a portionwise manner. The resulting mixture was stirred for about 2.5 hours at room temperature and then stirred at $45_{13}$C. for 30 minutes. Next, 2-methoxybenzylamine (20.7 ml, 158.7 mmol) was added and the reaction mixture was then stirred for 16 hours at room temperature.

The dioxane was removed under reduced pressure. The product was partitioned between ethyl acetate and water and was washed successively with 1 N hydrochloric acid, saturated sodium bicarbonate solution, water, and brine, followed by drying over sodium sulfate and removal of the solvent. Final crystallization from methanol yielded 52.2 g of homogeneous product as yellow crystals. Yield 80.8%. m.p. 157–160_C.

PREPARATION 2
Synthesis of 2-amino-3-(1H-indol-3-yl)-N-(2-methoxybenzyl)propanamide

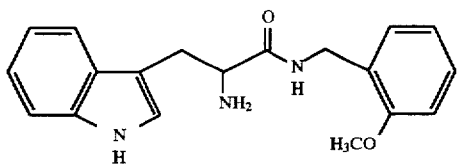

To a mixture of the 2-t-butoxycarbonylamino3-(1H-indol-3-yl)-N-(2-methoxybenzyl)propanamide prepared supra (25.1 g, 59.2 mmol) and anisole (12 ml, 110.4 mmol) at 0_C. was added dropwise an aqueous solution of trifluoroacetic acid (118 ml, 1.53 mol) in 50 ml of water. This mixture was stirred for one hour at 0_C., followed by stirring for about 2.5 hours at ambient temperature. The mixture was then refrigerated for about 16 hours.

The volatiles were removed under reduced pressure. The product was partitioned between ethyl acetate and saturated sodium bicarbonate solution and was then washed with water followed by brine and then dried over sodium sulfate. The solvents were removed in vacuo. Recrystallization from a 1:1 diethyl ether/cyclohexane solution yielded 18.0 g (94.2%) of homogeneous product as an off-white powder. m.p. 104–108_C.

PREPARATION 3
Preparation of 3-(1H-indol-3-yl)-2-(N-triphenylmethylamino)propanoic acid [N-trityltryptophan]

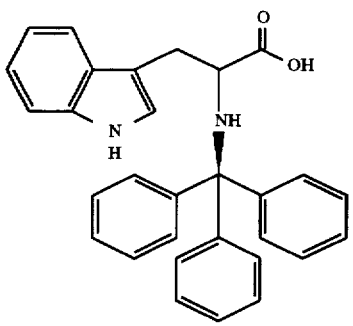

Chlorotrimethylsilane (70.0 ml, 0.527 mol) was added at a moderate rate to a stirring slurry of tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2x) and brine (2x) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure 3-(1H-indol3-yl)-2-(N-triphenylmethylamino) propanoic acid was isolated as a light tan solid in two crops giving a total of 79% yield.

PREPARATION 4
Preparation of 3-(1H-indol-3-yl)-N-(2-methoxybenzyl)-2-(N-triphenylmethylamino) propanamide

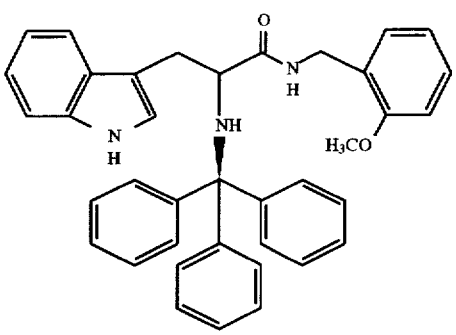

To a stirring solution of 3-(1H-indol-3-yl)-2-(N-triphenylmethylamino) propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0° C., were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2x), saturated sodium bicarbonate solution (2x), and brine (2x) was performed. The organic layer was dried over anhydrous sodium sulfate, filtered, and concentrated to dryness on a rotary evaporator. The title product was then filtered as a pink solid in two lots. Isolated 215.8 g (0.381 mol) of analytically pure material (95% yield).

Analysis for $C_{38}H_{35}N_3O_2$: Theory: C, 80.68; H, 6.24; N, 7.43; Found: C, 80.58; H, 6.42; N, 7.45.

PREPARATION 5
Preparation of 2-amino-3-(1H-indol-3-yl)-N-(2-methoxybenzyl) propanamide

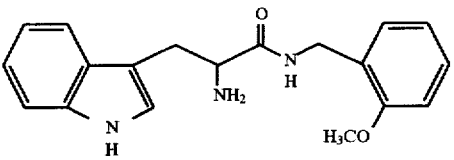

Formic acid (9.0 ml, 238.540 mmol) was added to a stirring solution of 3-(1H-indol-3-yl)-N-(2-methoxybenzyl)-2-(N-triphenylmethylamino) propanamide (14.11 g, 23.763 mmol) in anhydrous methylene chloride under a nitrogen atmosphere at 0° C. After 4 hours, the reaction mixture was concentrated to an oil on a rotary evaporator and redissolved

PREPARATION 6

Preparation of 2-amino-3-(1H-indol-3-yl)-N-(2-chlorobenzyl)propanamide

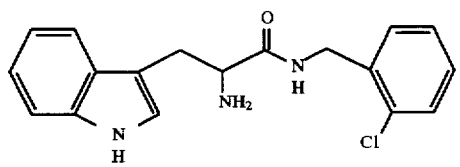

The title compound is prepared essentially as described above in Preparations 4 and 5 except that 2-chlorobenzylamine is employed instead of 2-methoxybenzylamine.

PREPARATION 7

Preparation of 2-t-butoxycarbonylamino-3-(1H-indol-3-yl)-N-(2-chlorobenzyl) propanamide

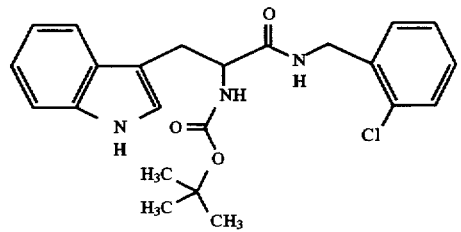

To a solution of N-(t-butoxycarbonyl)tryptophan (21.28 g, 70 mmol) in 140 ml of acetone was added triethylamine (9.76 ml, 7.08 g, 70 mmol) in a portionwise manner. The resulting mixture was stirred for about thirty-five minutes at room temperature and then stirred at 45_C. for 30 minutes under nitrogen. To the resulting mixture ethyl chloroformate (7.35 ml, 8.36 g, 77 mmol) was added with continued cooling and the reaction mixture was stirred for about one hour. Next, 2-chlorobenzylamine (9.30 ml, 10.9 g, 77 mmol) was added and the reaction mixture was then stirred until a white precipitate formed. The ice bath was removed and additional acetone was added. The reaction mixture was then stirred overnight.

The acetone was removed under reduced pressure. The residue was taken up in ethyl acetate (not all was soluble) and washed with dilute hydrochloric acid, followed by sodium hydroxide and then water. The solvents were removed by vacuum. After the addition of ether the reaction product was filtered and was washed with ether. Additional product was obtained by evaporating the ether filtrate. Yield >99%. NMR was consistent with the desired title product.

in diethyl ether and 1.0N hydrochloric acid. The aqueous layer was washed twice with diethyl ether and basified with sodium hydroxide to a pH greater than 12. The product was extracted out with methylene chloride (4x). The organic extracts were combined, dried over anhydrous sodium sulfate, filtered, and concentrated on a rotary evaporator to a white foam. The compound 3-(1H-indol-3-yl)-2-amino-N-(2-methoxybenzyl)propanamide (7.52 g, 21.397 mmols) was isolated giving a 90% yield. No further purification was necessary.

Analysis for $C_{19}H_{21}N_3O_2$; Theory: C,73.76; H, 7.49; N, 13.58; Found: C,72.15; H, 7.78; N, 12.77.

PREPARATION 8

Preparation of 2-amino-3-(1H-indol-3-yl)-N-(2-chlorobenzyl)propanamide

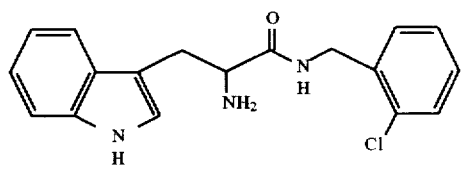

A stirring solution of 2-t-butoxycarbonylamino-3-(1H-indol-3-yl)-N-(2-chlorobenzyl)propanamide (6.00 g, 14 mmol) in 30 ml of 70% aqueous trifluoroacetic acid (21 ml trifluoroacetic acid, 9 ml water) was allowed to stir overnight at room temperature. The progress of this deprotection reaction was monitored by thin layer chromatography.

The solvents were removed in vacuo and the residue was taken up in acetonitrile, which was then removed by vacuum. The residue was partitioned between ether and 1N sodium hydroxide. The organic solvent was removed by vacuum and the residue was taken up in methylene chloride. The residue was removed by filtration and washed with additional methylene chloride.

The filtrate and basic washes were combined, extracted with methylene chloride, and dried over sodium sulfate. The solvents were removed in vacuo. Yield 4.3 grams (93%). NMR was consistent with the desired title intermediate.

PREPARATION 9

Preparation of 2-bromoacetamido-3-(1H-indol-3-yl)-N-(2-chlorobenzyl) propanamide

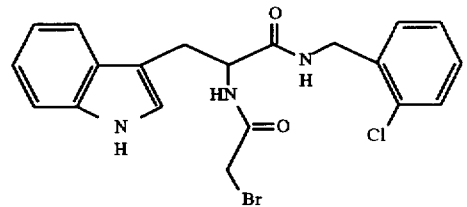

To a stirring solution of 2-amino-3-(1H-indol-3-yl)-N-(2-chlorobenzyl) propanamide (4.39 g, 13.3 mmol) and sodium carbonate (2.73 g, 26.6 mmol) in 100 ml of dry tetrahydrofuran was added bromoacetyl bromide (2.32 ml, 5.37 g, 26.6 mmol). The resulting mixture was then stirred at room temperature for about one hour. The progress of the reaction was monitored by thin layer chromatography.

The reaction mixture was stirred at room temperature overnight after the addition of more bromoacetyl bromide (about 0.5 ml). After the overnight stirring additional sodium carbonate (2.76 g) and bromoacetyl bromide (0.5 ml) were added and the reaction was stirred an additional five minutes.

The reaction mixture was then poured into 600 ml of ethyl acetate and was washed three times with water, followed by washes with dilute hydrochloric acid, water and brine. The organic fraction was dried over sodium sulfate and the solvents were removed by vacuum. Yield 5.24 g (88%). mp 182°–184° C. The NMR was consistent with the desired title intermediate.

PREPARATION 10

Preparation of 2-chloroacetamido-3-(1H-indol-3-yl)-N-(2-chlorobenzyl) propanamide

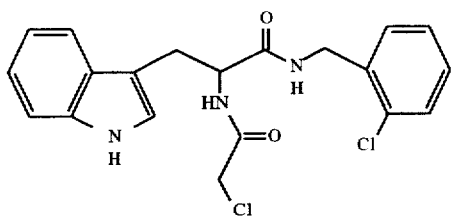

The title intermediate is prepared essentially as described in Preparation 9, supra, except that chloroacetyl chloride is employed in place of bromoacetyl bromide. mp 175–177.

Analysis for $C_{20}H_{19}Cl_2N_3O_2$; Theory: C, 59.42; H, 4.74; N, 10.39; Found: C, 59.21; H, 4.60; N, 10.12.

PREPARATION 11

Preparation of (R)-3-(1H-indol-3-yl)-2-(N-triphenylmethylamino) propanoic acid, N-methylmorpholine salt (N-trityl-D-tryptophan N-methylmorpholine salt).

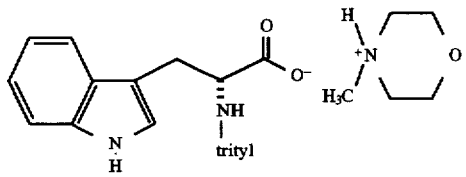

To a one liter 4 neck flask equipped with mechanical stirrer, condenser, probe, and stopper, were added D-tryptophan (40.0 g, 0.196 mol), acetonitrile (240 ml), and 1,1,1,3,3,3-hexamethyldisilazane (39.5 g, 0.245 mol). The resulting mixture was heated to 50°–60° C. and stirred until homogeneous. In a separate beaker trityl chloride (60.06 g, 0.215 mol) and acetonitrile (120 ml) were slurried. The slurry was added to the silylated tryptophan mixture and the beaker was rinsed with 40 ml of acetonitrile. To the reaction mixture N-methylmorpholine (23.7 ml, 21.8 g, 0.216 mol) was added and the resulting mixture was stirred for one hour. The progress of the reaction was monitored by chromatography.

After satisfactory progress, water (240 ml) was added dropwise to the reaction mixture and the resulting mixture was cooled to less than 10° C., stirred for thirty minutes, and filtered. The residue was washed with water, and then dried to obtain 108.15 grams (>99% yield) of the desired title product.

$^1$H NMR (DMSO-$d_6$) δ 2.70 (m, 1H), 2.83 (m, 2H), 3.35 (m, 1H), 6.92–7.20 (m, 12H), 7.30–7.41 (m, 8H), 10.83 (s, 1H), 11.73 (br s, 1H); Analysis for $C_{30}H_{26}N_2O_2$: Theory: C, 80.69; H, 5.87; N, 6.27; Found: C, 80.47; H, 5.92; N, 6.10.

Those intermediates of Formulae II and IV in which the stereochemistry is in the (S) configuration may be prepared essentially as described above, except that L-tryptophan is employed in place of the D-tryptophan employed therein. The resulting enantiomer may then be utilized as described below.

PREPARATION 12

Preparation of (R)-3-(1H-indol-3-yl)-N-(2-methoxybenzyl)-2-(N-triphenylmethylamino) propanamide.

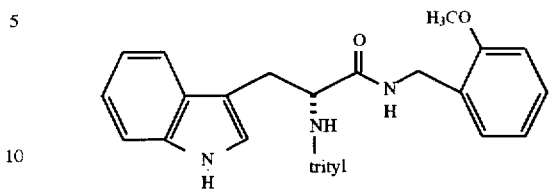

To a two liter 4 neck flask equipped with mechanical stirrer, condensor, and thermocouple, under a nitrogen atmosphere, were added N-trityl-D-tryptophan N-methylmorpholine salt (108.0 g, 0.196 mol), acetonitrile (800 ml), 2-chloro-4,6-dimethoxy-1,3,5-triazine (38.63 g, 0.22 mol), and N-methylmorpholine (29.1 ml). The resulting mixture was stirred at ambient temperature until homogeneous (about ten minutes).

After about one hour, 2-methoxybenzylamine (29 ml) was added. The resulting mixture was heated to 35° C. and maintained at that temperature overnight. The progress of the reaction was monitored by chromatography. Water (750 ml) was then added dropwise to the reaction mixture and the resulting mixture was cooled to less than 10° C., stirred for thirty minutes, and filtered. The residue was washed with water (about 100 ml), and then dried to obtain the desired title product. (Yield: 87% and 91% in two runs) FDMS 565 (M+).

$^1$H NMR (CDCl$_3$)δ 2.19 (dd, J=6.4 Hz, Δv=14.4 Hz, 1H), 2.64 (d, J=6.5 Hz, 1H), 3.19 (dd, J=4.3 Hz, Δv=14.4 Hz, 1H), 3.49 (m, 1H), 3.63 (s, 3H), 3.99 (dd, J=5.4 Hz, Δv=14.2 Hz, 1H), 4.25 (dd, J=7.1 Hz, Δv=14.2 Hz, 1H), 6.64 (d, J=2.1 Hz, 1H), 6.80 (d, J=8.2 Hz, 1H), 6.91 (t, J=7.4 Hz, 1H), 7.06–7.38 (m, 21 H), 7.49 (d, J=7.9 Hz, 1H), 7.75 (s, 1H); Analysis for $C_{38}H_{35}N_3O_2$: Theory: C, 80.68; H, 6.24; N, 7.43; Found: C, 80.65; H, 6.46; N, 7.50.

PREPARATION 13

Preparation of (R)-2-amino-3-(1H-indol-3-yl)-N-(2-methoxybenzyl) propanamide

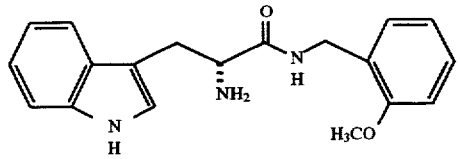

Formic acid (9.0 ml, 238.540 mmol) was added to a stirring solution of (R)-3-(1H-indol-3-yl)-N-(2-methoxybenzyl)-2-(N-triphenylmethylamino) propanamide (14.11 g, 23.763 mmol) in anhydrous methylene chloride under a nitrogen atmosphere at 0° C. After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound 3-(1H-indol-3-yl)-2-amino-N-(2-methoxybenzyl) propanamide (7.52 g, 21.397 mmols) was isolated giving a 90% yield. No further purification was necessary.

PREPARATION 14

Preparation of (R)-2-amino-3-(1H-indol-3-yl)-N-(4-chlorobenzyl) propanamide

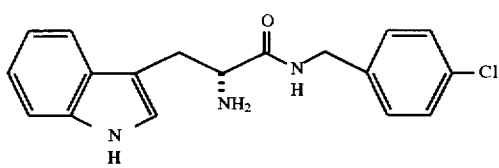

The title compound is prepared essentially as described above in Preparation 13 except that 4-chlorobenzylamine is employed instead of 2-methoxybenzylamine.

PREPARATION 15

Preparation of (R)-2-amino-3-(1H-indol-3-yl)-N-(4-methylbenzyl) propanamide

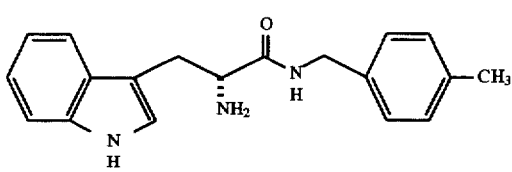

The title compound is prepared essentially as described above in Preparation 13 except that 4-methylbenzylamine is employed instead of 2-methoxybenzylamine.

PREPARATION 16

Preparation of (R)-2-amino-3-(1H-indol-3-yl)-N-(4-methylbenzyl) propanamide

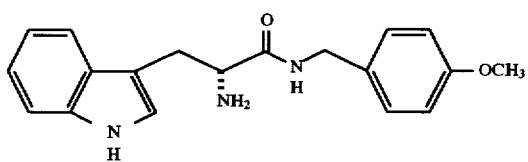

The title compound is prepared essentially as described above in Preparation 13 except that 4-methoxybenzylamine is employed instead of 2-methoxybenzylamine.

PREPARATION 17

Preparation of (R)-2 -amino-3-(1H-indol-3-yl)-N-(4-triflouromethylbenzyl) propanamide

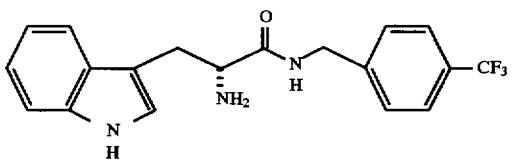

The title compound is prepared essentially as described above in Preparation 13 except that 4-trifluoromethylbenzylamne is employed instead of 2-methoxybenzylamine.

PREPARATION of 18

Preparation of (R)-2-amino-3-(1H-indol-3-yl)-N-(3,4-dichlorobenzyl) propanamide

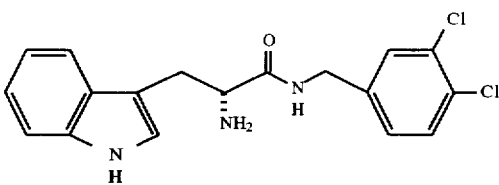

The title compound is prepared essentially as described above in Preparation 13 except that 3,4-dichlorobenzylamine is employed instead of 2-methoxybenzylamine.

PREPARATION 19

Preparation of (R)-2-amino-3-(1H-indol-3-yl)-N-(3,4-dimethylbenzyl) propanamide

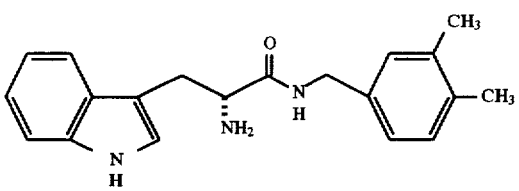

The title compound is prepared essentially as described above in Preparation 13 except that 3,4-dimethylbenzylamine is employed instead of 2-methoxybenzylamine.

PREPARATION 20

Preparation of (R)-2-amino-3-(1H-indol-3-yl)-N-(3,4-dimethoxybenzyl) propanamide

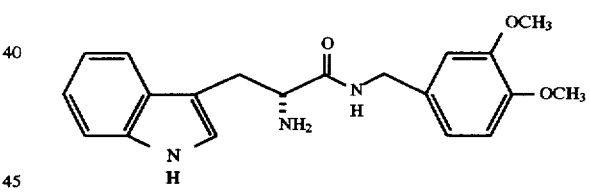

The title compound is prepared essentially as described above in Preparation 13 except that 3,4-dimethoxybenzylamine is employed instead of 2-methoxybenzylamine.

PREPARATION 21

Preparation of (R)-2-amino-3-(1H-indol-3-yl)-N-[3,4-bis(trifluoromethyl)benzyl]propanamide

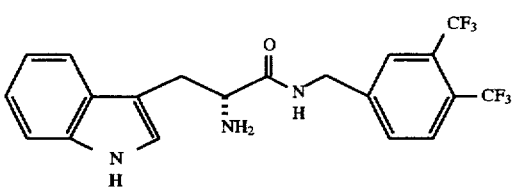

The title compound is prepared essentially as described above in Preparation 13 except that 3,4-bis(trifluoromethyl) benzylamine is employed instead of 2-methoxybenzylamine.

PREPARATION 22
Preparation of (R)-2-amino-3-(1H-indol-3-y)-N-(2-methylbenzyl) propanamide

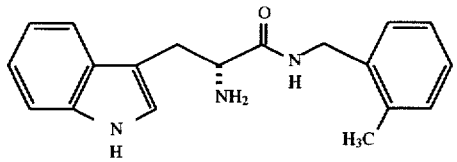

The title compound is prepared essentially as described above in Preparation 13 except that 2-methylbenzylamine is employed instead of 2-methoxybenzylamine.

PREPARATION 23
Preparation of (R)-2-amino-3-(1H-indol-3yl)-N-(2-methylthiobenzyl) propanamide

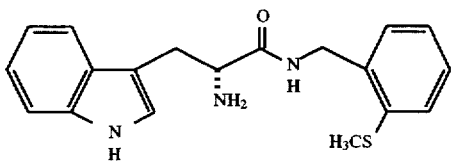

The title compound is prepared essentially as described above in Preparation 13 except that 2-methylthiobenzylamine is employed instead of 2-methoxybenzylanine.

PREPARATION 24
Preparation of (R)-2-amino-3-(1H-indol-3-yl)-N-(2-trifluoromethylphenyl) propanamide

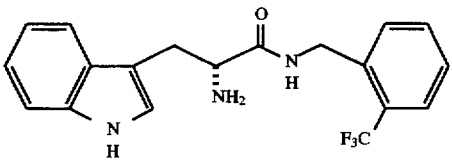

The title compound is prepared essentially as described above in Preparation 13 except that 2-trifluoromethylbenzylamine is employed instead of 2-methoxybenzylamine.

The compounds of Formulae III and V may be prepared by methods well known to one of ordinary skill in the art. A majority of the starting indoles are commercially available, however they may be prepared by the Fischer indole synthesis (Robinson, THE FISCHER INDOLE SYNTHESIS, Wiley, N.Y., 1983)

The indoles are condensed with 4-piperidone .HCl.H$_2$O in the presence of a suitable base to give the corresponding 3-(1,2,3,6-tetrahydro-4-pyridinyl)-1H-indoles as illustrated in the following scheme.

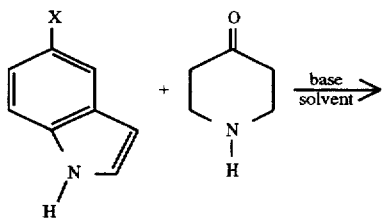

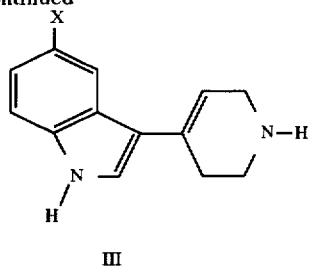

III

The reaction is performed by first dissolving an excess of the base, typically sodium or potassium hydroxide, in a lower alkanol, typically methanol or ethanol. The indole and two equivalents of 4-piperidone. HCl.H$_2$O are then added and the reaction refluxed for 8–72 hours. The resulting 3-(1,2,2,6-tetrahydro-4-pyridinyl)-1H-indoles may be isolated from the reaction mixture by the addition of water. Compounds which precipitate may be isolated directly by filtration while others may be extracted with a water immiscible solvent such as ethyl acetate or dichloromethane. The compounds recovered may be used directly in subsequent steps or first purified by silica gel chromatography or recrystallization from a suitable solvent.

The 3-(1,2,5,6-tetrahydro-4-pyridinyl)-1H-indoles may next be hydrogenated to give the corresponding 3-(piperidin-4yl)-1H-indoles as shown below.

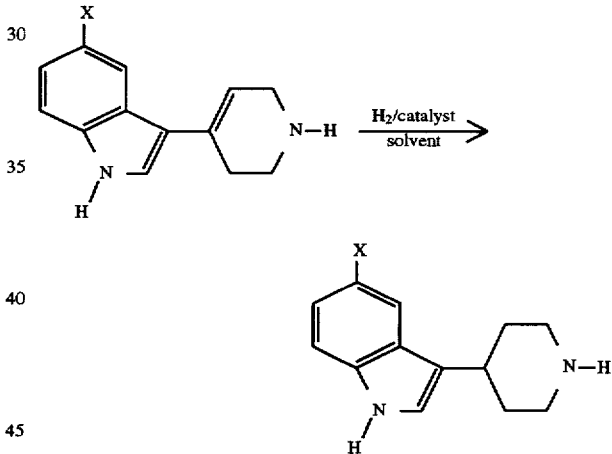

The catalyst may be a precious metal catalyst such as platinum oxide, or palladium or platinum on a suitable support such as carbon. When X is a functional group that is labile to hydrogenolysis, such as halo or benzyloxy, a deactivated catalyst such as sulfided platinum on carbon or a mixed catalyst system of sulfided platinum on carbon with platinum oxide may be used to prevent hydrogenolysis. The solvent may consist of a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. The 3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography or recrystallization from a suitable solvent.

All of the 3-[1,2,3,6-tetrahydro-4-pyridinyl]-1H-indoles useful as intermediates for compounds of this invention may be prepared as described in the following procedure.

PREPARATION 25

5-bromo-3-[1,2,3,6-tetrahydro-4-pyridinyl]-1H-indole

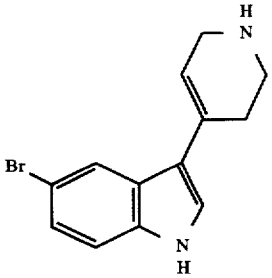

To a solution of 4.29 gm (77 mmol) potassium hydroxide in 50 ml methanol were added 5.0 gm (26 mmol) 5-bromoindole and 7.84 gm (51 mmol) 4piperidone .HCl.H₂O and the reaction mixture was stirred for 18 hours at reflux under a nitrogen atmosphere. The reaction mixture was cooled to ambient temperature, diluted with 500 ml water and the mixture extracted well with dichloromethane. The combined organic extracts were washed with water followed by saturated aqueous sodium chloride and dried over sodium sulfate. The remaining organics were concentrated under reduced pressure to give 6.23 gm (86.5%) of the title compound as a yellow oil.

¹H-NMR (DMSO-d₆): δ 8.00 (s,1H); 7.40 (s,1H); 7.30 (d, 1H); 7.20 (d, 1H); 6.10 (s, 1H); 3.35 (br s, 2H); 2.85 (m, 2H); 2.35 (br s, 2H).

All of the 3.[piperidine-4-yl].1H.indoles useful as intermediates for compounds of this invention may be prepared as described in the following procedure.

PREPARATION 26

5-bromo-3-[piperidine-4-yl]-1H-indole

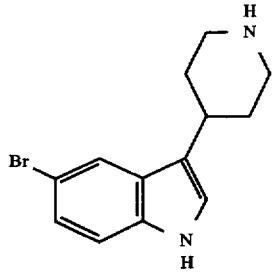

To a solution of 13.61 gm (49 mmol) 5-bromo 3-[1,2,3,6-tetrahydro-4-pyridinyl]-1H-indole in 75 ml 2:1 tetrahydro-furan ethyl acetate were added 8.0 gm 3% sulfided platinum on carbon and 4.0 gm platinum oxide. The reaction mixture was hydrogenated with an initial hydrogen pressure of 60 p.s.i. at 40° C. for 18 hours and then at ambient temperature for 30 hours. The reaction mixture was filtered and the filtrate concentrated under reduced pressure to give 10.33 gm (75.6%) of the title compound as a light yellow solid.

MS(m/e): 278(M⁺); ¹H-NMR(DMSO-d₆): d10.6 (s, 1H); 7.2 (d, 1H); 7.05 (s, 2H); 6.7 (d, 1H); 3.15 (s, 1H); 3.05 (s, 1H); 2.8 (m, 3H), 1.95 (s, 1H); 1.85 (s, 1H); 1.6 (m 2H).

PREPARATION 27

5-carboxamidoindole

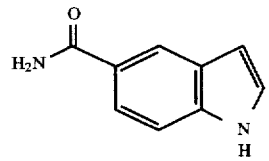

To a solution of 8.06 gm (50 mmol) indole-5-carboxylic acid in 150 ml dimethylformamide were added 8.11 gm (50 mmol) carbonylidiimidazole and the reaction mixture stirred at ambient temperature for 3 hours. The reaction mixture was then added dropwise to 150 ml concentrated ammonium hydroxide and the reaction mixture was stirred for 18 hours at ambient temperature. The reaction mixture was concentrated under reduced pressure to give a viscous oil which was subjected to silica gel chromatography, eluting with a gradient of dichloromethane containing 0–10% methanol. Fractions shown to contain product were combined and concentrated under reduced pressure to give the title compound as an oil which crystallizes upon standing.

¹H-NMR(CDCl₃): d8.18 (s, 1H); 7.74 (d, 1H); 7.45 (d, 1H); 7.35 (s, 1H); 6.65 (s, 1H).

The other compounds of Formula III may be prepared essentially as described above using commercially available starting materials. The compounds of Formula V may be prepared from the corresponding compound of Formula III by haloacetylation as described in Preparation 9.

EXAMPLE 1

Preparation of (R)-2-{[4-[5-[(benzylamino)carbonyl]indol-3-yl]-1,2,3,6-tetrahydropyridin1-yl]acetamido}-3-(1H-indol-3-yl)-N-(2-methoxybenzyl) propanamide

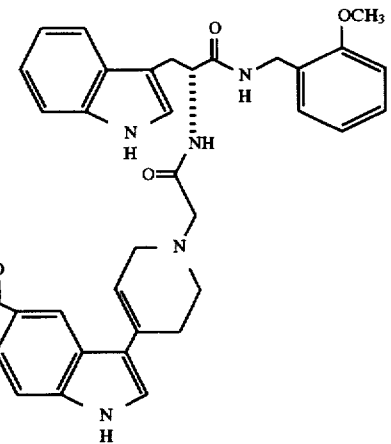

A 10 ml tear drop flask is charged with 2-[(2-bromo)acetyl]amino-3-(1H-indol-3-yl)-1-[N-(2-methoxybenzyl)acetyl]propanamide (0.10 g, 0.2 mmol), powdered potassium carbonate (0.117 g, 0.84 mmol) and 4-[5-[(benzylamino) carbonyl]indol-3-yl]-1,2,3,6-tetrahydropyridine (0.078 g, 0.212 mmol). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

The following Examples are prepared essentially as described in Example 1, except that other intermediates are employed.

EXAMPLE 2

Preparation of (R)-2-{[4-[5-(hydroxy)indol-3-yl]piperidin1-yl]acetamido}-3-(1H-indol-3-yl)-N-(2-methoxybenzyl)propanamide

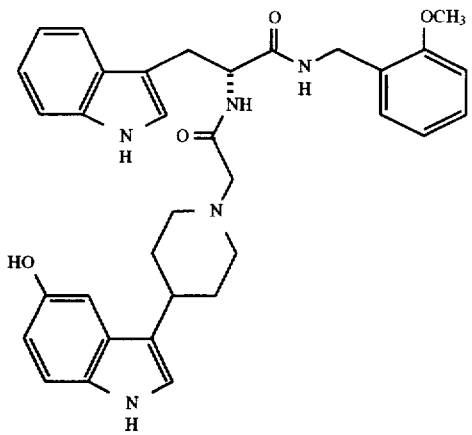

A 10 ml round bottom flask is charged with 2-[(2-bromo)acetyl]amino-3-(1H-indol-3-yl)-1-[N-(2-methoxybenzyl)acetylamino]propanamide (0.10 g, 0.212 mmol), powdered potassium carbonate (0.117 g, 0.84 mmol) and 4-[5-(hydroxy)indol-3-yl]piperidine (0.055 g, 0.212 mmol). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into ice water and the solids are collected by vacuum filtration. The solids are dried in a vacuum oven overnight to yield the desired title product, which is further purified by thin layer chromatography.

EXAMPLE 3

Preparation of (R)-2-{[4-[5-(fluoro)indol-3-yl]-1,2,3,6-tetrahydropyridin-1-yl]acetamido}-3-(1H-indol-3-yl)-N-(2-methoxybenzyl)propanamide

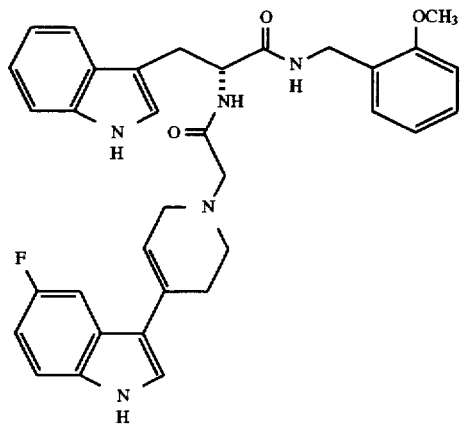

EXAMPLE 4

Preparation of (R)-2-{[4-[5-(methoxy)indol-3-yl]-1,2,3,6-tetrahydropyridin-1-yl]acetamido}-3-(1H-indol-3-yl)-N-(2-methoxybenzyl)propanamide

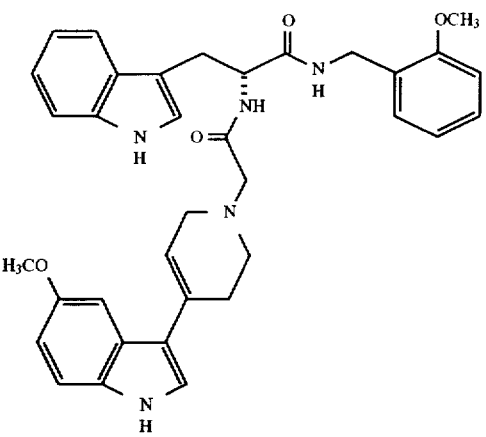

EXAMPLE 5

Preparation of (R)-2-{[4-[5-(fluoro)indol-3-yl]piperidin1-yl]acetamido}-3-(1H-indol-3-yl)-N-(2-methoxybenzyl)propanamide

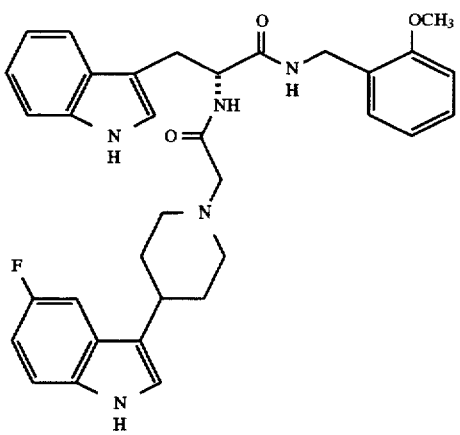

EXAMPLE 6

Preparation of (R)-2-{[4-[5-(chloro)indol-3-yl]piperidin1-yl]acetamido}-3-(1H-indol-3-yl)-N-(2-methoxybenzyl)propanamide

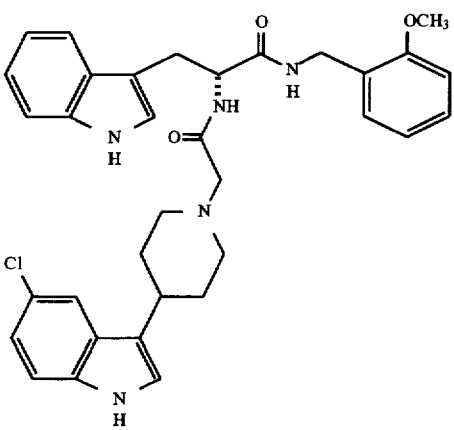

EXAMPLE 7

Preparation of (R)-2-{[4-[5-(4-fluorobenzamido)indol-3-yl] piperidin-1-yl]acetamido}-3-(1H-indol-3-yl)-N-(2-methoxybenzyl)propanamide

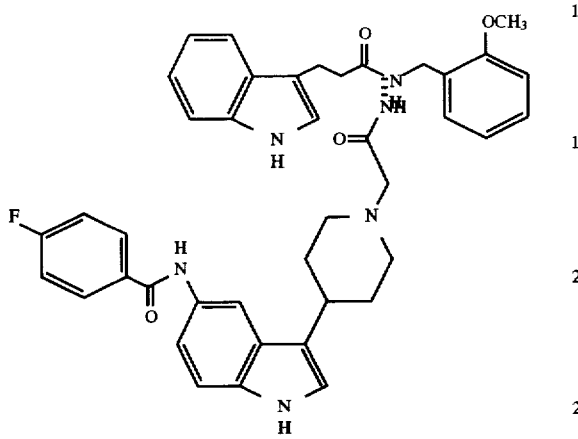

EXAMPLE 8

Preparation of (R)-2-{[4-[5-(cyano)indol-3-yl]1,2,3,6-tetrahydropyridin-1-yl]acetamido}-3-(1H-indol-3-yl)-N-(2-methoxybenzyl)propanamide

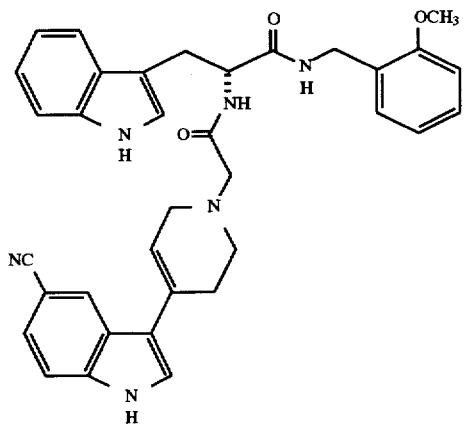

EXAMPLE 9

Preparation of (R)-2-{[4-[5-(chloro)indol-3-yl]-1,2,3,6-tetrahydropyridin-1-yl]acetamido}-3-(1H-indol-3-yl)-N-(2-methoxybenzyl)propanamide

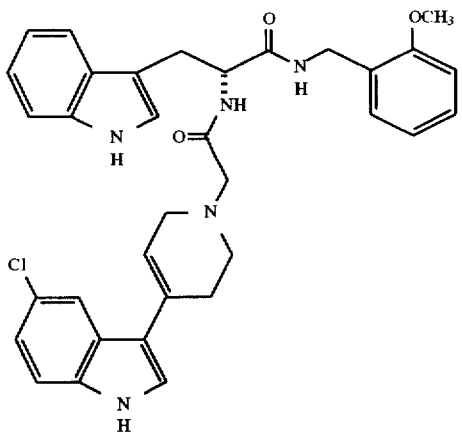

Using procedures analogous to those of Examples 1 through 9 and the intermediates described in the Preparations supra, the following other compounds of Formula I are prepared: (R)-2-{[4-[5-(4-fluorobenzamido) indol-3-yl] piperidin-1-yl]acetamido}-3-(1H-indol-3-yl)-N-(2-methoxybenzyl) propanamide; (R)-2-{[4-[5-(fluoro)indol-3-yl]piperidin-1-yl]acetamido}-3-(1H-indol-3-yl)-N-(2-methoxybenzyl)propanamide; (R)-2-{[4-[5-(fluoro)indol-3-yl]-1,2,3,6-tetrahydropyridin-1-yl]acetamido}-3-(1H-indol-3-yl)-N-(2-methoxybenzyl)propanamide; (R)-2-{[4-[5-(methoxy)indol-3-yl]-1,2 ,3,6-tetrahydropyridin-1-yl] acetamido}-3-(1H-indol-3-yl)-N-(2-methoxybenzyl) propanamide; (R)-2-{[4-[5-(hydroxy)indol-3-yl]piperidin-1-yl]acetamido}-3-(1H-indol-3-yl)-N-(2-methoxybenzyl) propanamide; (R)-2-{[4-[5-(chloro)indol-3-yl]piperidin-1-yl]acetamido}-3-(1H-indol-3-yl)-N-(2-methoxybenzyl propanamide; (R)-2-{[4-[5-[(benzylamino)carbonyl]indol-3-yl]-1,2,3,6-tetrahydropyridin-1-yl]acetamido}-3-(1H-indol-3-yl)-N-(2-methoxybenzyl) propanamide; (R)-2-{[4-[5-(cyano)indol-3-yl]-1,2,3, 6-tetrahydropyridin-1-yl] acetamido}-3-(1H-indol-3-yl)-N-(2-methoxybenzyl) propanamide; (R)-2-{[4-[5-(4-fluorobenzamido)indol-3-yl] piperidin-1-yl]acetamido}-3-(1H-indol-3-yl)-N-(2-chlorobenzyl) propanamide; (R)-2-{[4-[5-(fluoro)indol-3-yl]piperidin-1-yl]acetamido}-3-(1H-indol-3-yl)-N-(2-chlorobenzyl)propanamide; (R)-2-{[4-[5-(fluoro)indol-3-yl]-1,2 ,3,6-tetrahydropyridin-1-yl]acetamido}-3-(1H-indol-3-yl)-N-(2-chlorobenzyl)propanamide; (R)-2-{[4-[5-(methoxy)indol-3-yl]-1,2,3,6-tetrahydropyridin-1-yl] acetamido}-3-(1H-indol-3-yl)-N-(2-chlorobenzyl) propanamide; (R)-2-{[4-[5-(hydroxy)indol-3-yl]piperidin-1-yl]acetamido}-3-(1H-indol-3-yl)-N-(2-chlorobenzyl) propanamide; (R)-2-{[4-[5-(chloro)indol-3-yl]piperidin-1-yl]acetamido}-3-(1H-indol-3-yl)-N-(2-chlorobenzyl) propanamide; (R)-2-{[4-[5-[(benzylamino)carbonyl]indol-3-yl]-1,2,3,6-tetrahydropyridin-1-yl]acetamido}-3-(1H-indol-3-yl)-N-(2-chlorobenzyl) propanamide; (R)-2-{[4-[5-(cyano)indol-3-yl]-1,2,3, 6-tetrahydropyridin-1-yl] acetamido}-3-(1H-indol-3-yl)-N-(2-chlorobenzyl) propanamide; (R)-2-{[4-[5-(4-fluorobenzamido)indol-3-yl] piperidin-1-yl]acetamido}-3-(1H-indol-3-yl)-N-(2-methylbenzyl) propanamide; (R)-2-{[4-[5-(fluoro)indol-3-yl]piperidin-1-yl]acetamido}-3-(1H-indol-3-yl)-N-(2-methylbenzyl)propanamide; (R)-2-{[4-[5-(fluoro)indol-3-yl]-1,2 ,3,6-tetrahydropyridin-1 -yl] acetamido}-3-(1H-indol- 3-yl)-N-(2-methylbenzyl)propanamide; (R)-2-{[4-[5-(methoxy)indol-3-yl]-1,2 ,3,6-tetrahydropyridin-1-yl] acetamido}-3-(1H-indol-3-yl)-N-(2-methylbenzyl)

propanamide; (R)-2-{|4-|5-(hydroxy)indol-3-yl|piperidin-1-yl|acetamido}-3-(1H-indol-3-yl)-N-(2-methylbenzyl) propanamide; (R)-2-{|4-|5-(chloro)indol-3-yl|piperidin-1-yl|acetamido}-3-(1H-indol-3-yl)-N-(2-methylbenzyl) propanamide; (R)-2-{|4-|5-|(benzylamino)carbonyl|indol-3-yl|-1,2,3,6-tetrahydropyridin-1-yl|acetamido}-3-(1H-indol-3-yl)-N-(2-methylbenzyl) propanamide; (R)-2-{|4-|5-(cyano)indol-3-yl|-1,2,3, 6-tetrahydropyridin-1-yl| acetamido}-3-(1H-indol-3-yl)-N-(2-methylbenzyl) propanamide; (R)-2-{|4-|5-(4-fluorobenzamido)indol-3-yl| piperidin-1-yl|acetamido}-3-(1H-indol-3-yl)-N-(2-trifluoromethylbenzyl) propanamide; (R)-2-{|4-|5-(fluoro) indol-3-yl|piperidin-1-yl|acetamido}-3-(1H-indol-3-yl)-N-(2-trifluoromethylbenzyl) propanamide; (R)-2-{|4-|5-(fluoro)indol-3-yl|-1,2,3,6-tetrahydropyridin-1-yl| acetamido}-3-(1H-indol-3-yl)-N-(2-trifluoromethylbenzyl) propanamide; (R)-2-{|4-|5-(methoxy)indol-3-yl|-1,2,3,6-tetrahydropyridin-1-yl|acetamido}-3-(1H-indol-3-yl)-N-(2-trifluoromethylbenzyl) propanamide; (R)-2-{|4-|5-(hydroxy)indol-3-yl|piperidin-1-yl|acetamido}-3-(1H-indol-3-yl)-N-(2-trifluoromethylbenzyl) propanamide; (R)-2-{|4-|5-(chloro)indol-3-yl|piperidin-1-yl|acetamido}-3-(1H-indol-3-yl)-N-(2-trifluoromethylbenzyl) propanamide; (R)-2-{|4-|5-|(benzylamino) carbonyl|indol-3-yl|-1,2,3,6-tetrahydropyridin-1-yl|acetamido}-3-(1H-indol-3-yl)-N-(2-trifluoromethylbenzyl)propanamide; (R)-2-{|4-|5-(cyano)indol-3-yl|-1,2,3,6-tetrahydropyridin-1 -yl|acetamido}-3-(1H-indol-3-yl)-N-(2-trifluoromethylbenzyl)propanamide; (R)-2-{|4-|5-(4-fluorobenzamido) indol-3-yl|piperidin-1-yl| acetamido}-3-(1H-indol-3-yl)-N-(3,4-dimethoxybenzyl) propanamide; (R)-2-{|4-|5-(fluoro)indol-3-yl|piperidin-1-yl|acetamido}-3-(1H-indol-3-yl)-N-(3,4-dimethoxybenzyl) propanamide; (R)-2-{|4-|5-(fluoro)indol-3-yl|-1,2,3, 6-tetrahydropyridin-1 -yl|acetamido}-3-(1H-indol-3-yl)-N-(3,4-dimethoxybenzyl) propanamide; (R)-2-{|4-|5-(methoxy)indol-3-yl|-1,2,3, 6-tetrahydropyridin-1-yl| acetamido}-3-(1H-indol-3-yl)-N-(3,4-dimethoxybenzyl) propanamide; (R)-2-{|4-|5-hydroxy)indol-3-yl|piperidin-1-yl|acetamido}-3-(1H-indol-3-yl)-N-(3,4-dimethoxybenzyl) propanamide; (R)-2{|4-|5-(chloro)indol-3-yl|piperidin-1-yl|acetamido}-3-(1H-indol-3-yl)-N-(3,4-dimethoxybenzyl) propanamide; (R)-2-{|4-|5-|(benzylamino) carbonyl|indol-3-yl|-1,2,3,6-tetrahydropyridin-1-yl|acetamido}-3-(1H-indol-3-yl)-N-(3,4-dimethoxybenzyl)propanamide; (R)-2{ |4-|5-(cyano)indol-3-yl|-1,2,3,6-tetrahydropyridin-1-yl| acetamido}-3-(1H-indol-3-yl)-N-(3,4-dimethoxybenzyl) propanamide; (R)-2-{|4-|5-(4-fluorobenzamido) indol-3-yl| piperidin-1 -yl|acetamido}-3-(1H-indol-3-yl)-N-(3,4-dichlorobenzyl)propanamide; (R)-2-{|4-|5-(fluoro)indol-3-yl|piperidin-1-yl|acetamido}-3-(1H-indol-3-yl)-N-(3,4-dichlorobenzyl)propanamide; (R)-2-{|4-|5-(fluoro)indol-3-yl|-1,2,3,6-tetrahydropyridin-1-yl|acetamido}-3-(1H-indol-3-yl)-N-(3,4-dichlorobenzyl)propanamide; (R)-2-{|4-|5-(methoxy) indol-3-yl|-1,2,3,6-tetrahydropyridin-1-yl] acetamido}-3-(1H-indol-3-yl)-N-(3,4-dichlorobenzyl) propanamide; (R)-2-{|4-|5-(hydroxy) indol-3-yl|piperidin-1-yl|acetamido}-3-(1H-indol-3-yl)-N-(3,4-dichlorobenzyl) propanamide; (R)-2-{|4-|5-(chloro)indol-3-yl|piperidin-1-yl|acetamido}-3-(1H-indol-3-yl)-N-(3,4-dichlorobenzyl) propanamide; (R)-2-{|4-|5-|(benzylamino)carbonyl|indol-3-yl|-1,2,3,6-tetrahydropyridin-1-yl|acetamido}-3-(1H-indol-3-yl)-N-(3,4-dichlorobenzyl)propanamide; (R)-2-{|4-|5-(cyano)indol-3-yl|-1,2,3,6-tetrahydropyridin-1-yl| acetamido}-3-(1H-indol-3-yl)-N-(3,4-dichlorobenzyl) propanamide; (R)-2-{|4-|5-(4-fluorobenzamido) indol-3-yl| piperidin-1-yl|acetamido}-3-(1H-indol-3-yl)-N-(3,4,5-trimethylbenzyl)propanamide; (R)-2-{|4-|5-(fluoro)indol-3-yl|piperidin-1yl|acetamido}-3-(1H-indol-3-yl)-N-(3,4,5-trimethylbenzyl) propanamide; (R)-2-{|4-|5-(fluoro)indol-3-yl|-1,2,3, 6-tetrahydropyridin-1-yl|acetamido}-3-(1H-indol-3-yl)-N-(3,4,5-trimethylbenzyl) propanamide; (R)-2-{ |4-|5-(methoxy)indol-3-yl|-1,2,3, 6-tetrahydropyridin-1-yl| acetamido}-3-(1H-indol-3-yl)-N-(3,4,5-trimethylbenzyl) propanamide; (R)-2-{|4-|5-(hydroxy)indol-3-yl|piperidin-1-yl|acetamido}-3-(1H-indol-3-yl)-N-(3,4,5-trimethylbenzyl)propanamide; (R)-2{|4-|5-(chloro)indol-3-yl|piperidin-1-yl|acetamido}-3-(1H-indol-3N-(3,4,5-trimethylbenzyl)propanamide; (R)-2-{|4-|5-|(benzylamino) carbonyl|indol-3-yl|-1,2,3,6-tetrahydropyridin-1-yl| acetamido}-3-(1H-indol-3-yl)-N-(3,4,5-trimethylbenzyl) propanamide; (R)-2-{|4-|5-(cyano)indol-3-yl|-1,2,3,6-tetrahydropyridin-1-yl|acetamido}-3-(1H-indol-3-yl)-N-(3, 4,5-trimethylbenzyl)propanamide; (R)-2-{|4-|5-(4-fluorobenzamido) indol-3-yl|piperidin-1-yl|acetamido}-3-(1H-indol-3-yl)-N-(3,5-dimethoxybenzyl) propanamide; (R)-2-{|4-|5-(fluoro)indol-3-yl|piperidin-1-yl|acetamido}-3-(1H-indol-3-yl)-N-(3,5-dimethoxybenzyl) propanamide; (R)-2-{|4-|5-(fluoro)indol-3-yl|-1,2,3, 6-tetrahydropyridin-1 -yl| acetamido}-3-(1H-indol-3-yl)-N-(3,5-dimethoxybenzyl) propanamide; (R)-2-{|4-|5-(methoxy) indol-3-yl|-1,2,3, 6-tetrahydropyridin-1-yl|acetamido}-3-(1H-indol-3-yl)-N-(3,5-dimethoxybenzyl) propanamide; (R)-2-{|4-|5-(hydroxy)indol-3 -yl|piperidin-1-yl| acetamido}-3-(1H-indol-3-yl)-N-(3,5-dimethoxybenzyl) propanamide; (R)-2-{|4-|5-(chloro)indol-3-yl|piperidin-1-yl|acetamido}-3-(1H-indol-3-yl)-N-(3,5-dimethoxybenzyl) propanamide; (R)-2-{|4-|5-|(benzylamino) carbonyl|indol-3-yl|-1,2,3,6-tetrahydropyridin-1-yl|acetamido}-3-(1H-indol-3-yl)-N-(3,5-dimethoxybenzyl)propanamide; and (R)-2-{|4-|5-(cyano)indol-3-yl|-1,2,3,6-tetrahydropyridin-1-yl| acetamido}-3-(1H-indol-3-yl)-N-(3,5-dimethoxybenzyl) propanamide. It should be readily apparent to one skilled in the art that a large number of other compounds of Formula I may be prepared using other intermediates prepared essentially as described infra. Such other compounds of Formula I are within the scope of this invention.

The compounds of Formula I are useful as tachykinin receptor antagonists. The biological activity of the compounds of the present invention is evaluated employing an initial screening assay which rapidly and accurately measured the binding of the tested compound to known NK-1 and NK-2 receptor sites. Assays useful for evaluating tachykinin receptor antagonists are well known in the art. See. e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays are performed using a derivative of a previously published protocol. D. G. Payan, et al., *Journal of Immunology*, 133:3260–3265 (1984). In this assay an aliquot of IM9 cells (1×10$^6$ cells/tube in RPMI 1604 medium supplemented with 10% fetal calf serum) is incubated with 20 pM $^{125}$I-labeled substance P in the presence of increasing competitor concentrations for 45 minutes at 4° C.

The IM9 cell line is a well-characterized cell line which is readily available to the public. See e.g., *Annals of the New York Academy of Science*, 190: 221–234 (1972); *Nature* (London), 251:443–444 (1974); *Proceedings of the National Academy of Sciences (USA)*, 71:84–88 (1974). These cells are routinely cultured in RPMI 1640 supplemented with 50 µg/ml gentamicin sulfate and 10% fetal calf serum.

The reaction is terminated by filtration through a glass fiber filter harvesting system using filters previously soaked for 20 minutes in 0.1% polyethylenimine. Specific binding of labeled substance P is determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, are grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures are dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells are pooled and centrifuged at 1,000 RPM for 10 minutes in a clinical centrifuge. Membranes are prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets are washed once using the above procedure, and the final pellets are resuspended in 100–120 ml 50 mM Tris buffer, pH 7.4, and 4 ml aliquots stored frozen at –70° C. The protein concentration of this preparation is 2 mg/ml.

For the receptor binding assay, one 4-ml aliquot of the CHO-hNK-2R membrane preparation is suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) is used per sample. The radioactive ligand is [$^{125}$I]iodohistidyl-neurokinin A (New England Nuclear, NEX-252), 2200 Ci/mmol. The ligand is prepared in assay buffer at 20 nCi per 100 µl; the final concentration in the assay is 20 pM. Non-specific binding is determined using 1 µM eledoisin. Ten concentrations of eledoisin from 0.1 to 1000 nM are used for a standard concentration-response curve.

All samples and standards are added to the incubation in 10 µl dimethylsulfoxide (DMSO) for screening (single dose) or in 5 µl DMSO for IC$_{50}$ determinations. The order of additions for incubation is 190 or 195 µl assay buffer, 200 µl homogenate, 10 or 5 µl sample in DMSO, 100 µl radioactive ligand. The samples are incubated 1 hour at room temperature and then filtered on a cell harvester through filters which had been presoaked for two hours in 50 mM Tris buffer, pH 7.7, containing 0.5% BSA. The filter is washed 3 times with approximately 3 ml of cold 50 mM Tris buffer, pH 7.7. The filter circles are then punched into 12×75 mm polystyrene tubes and counted in a gamma counter.

As the compounds of Formula I are effective tachykinin receptor antagonists, these compounds are of value in the treatment of a wide variety of clinical conditions which are characterized by the presence of an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt, solvate or prodrug thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; atherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative colitis, Crohn's disease, emesis, and irritable bowel syndrome; incontinence; disorders of blood flow caused by vasodilation; and pain or nociception, for example, that attributable to or associated with any of the foregoing conditions or the transmission of pain in migraine.

Many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

In addition to the above indications the compounds of Formula I are particularly useful in the treatment of emesis, including acute, delayed, or anticipatory emesis, such as emesis induced by chemotherapy, radiation, toxins, pregnancy, vestibular disorders, motion, surgery, migraine, and variations in intercranial pressure. Most especially, the compounds of Formula I are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates, and otehr compounds with an alkylating action, such as nitrosoureas, cisplatin, and dacarbazine; antimetabolites, for example, folic acid, purine, or pyrimidine antagonists; mitotic inhibitors, for example vinca alkaloids and derivatives of podophyllotoxin; and cytotoxic antibiotics.

Particular examples of chemotherapeutic agents are described, for instance, by D. J. Stewart in NAUSEA AND VOMITING: RECENT RESEARCH AND CLINICAL ADVANCES, (J. Kucharczyk, et al., eds., 1991), at pages 177–203. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin, and chlorambucil. R. J. Gralla, et al., *Cancer Treatment Reports*, 68:163–172 (1984).

The compounds of Formula I are also of use in the treatment of emesis induced by radiation, including radiation therapy such as in the treatment of cancer, or radiation sickness; and in the treatment of post-operaive nausea and vomiting.

It will be appreciated that a compound of Formula I may be presented together with another therapeutic agent as a combined preparation for simultaneous, separate, or sequential use for the relief of emesis. Such combined preparations may be, for example, in the form of a twin pack.

As one example, it may be desirable to employ a compound of Formula I in conjunction with a bronchodilator (such as a $\beta_2$-adrenergic receptor antagonist) for the treatment of asthma. The present invention also provides, therefore, a composition comprising a compound of Formula I, a bronchodilator, and a pharmaceutically acceptable carrier.

Recent reports have demonstrated that the co-administration of an NK-1 antagonist and an NK-2 antagonist has a synergistic advantage over either alone. United Kingdom Patent Application GB 2,274,777 A, published Aug. 10, 1994. This line of reasoning would suggest, therefore, that a compound of Formula I which has antagonist activity at both the NK-1 and NK-2 receptors, even though neither such activity is optimal when compared to the other compounds of Formula I, may be preferable to a compound having optimal activity at one or the other receptor.

The compounds of the present invention also have activity as serotonin agonists. The biological efficacy of a compound believed to be effective as a serotonin agonist may be confirmed by first employing an initial screening assay which rapidly and accurately measures the binding of the test compound to one or more serotonin receptors. Once the binding of the test compound to one or more serotonin receptors is established, the in vivo activity of the test compound on the receptor is established. Assays useful for evaluating serotonin agonists are well known in the art. See, e.g., E. Zifa and G. Fillion, infra; D. Hoyer, et al., infra, and the references cited therein.

Many serotonin binding receptors have been identified. These receptors are generally grouped into seven classes on the basis of their structure and the pharmacology of the receptor as determined by the binding efficiency and drug-related characteristics of numerous serotonin receptor-binding compounds. In some of the groups several subtypes have been identified. [For a relatively recent review of 5-hydroxytryptamine receptors, see, E. Zifa and G. Fillion, *Pharamcological Reviews*, 44:401–458 (1992); D. Hoyer, et al., *Pharamcological Reviews*, 46:157–203 (1994).] Table I, infra, lists the seven classes of serotonin receptors as well as several known subtypes. This table also provides the physiological distribution of these receptors as well as biological responses mediated by the receptor class or subtype, if any such response is known. This table is derived from D. Hoyer, et al., "VII. International Union of Pharmacology Classification of Receptors for 5-Hydroxytryptamine (Serotonin)", *Pharmacological Reviews*, 46:157–203 (1994), a publication of the Serotonin Club Receptor Nomenclature Committee of the IUPHAR Committee for Receptor Nomenclature.

The Hoyer, et al., reference describes for each class or subtype one or more compounds which have efficacy as antagonists or agonists for the receptor.

The 5-HT$_1$ family includes subtypes which can be grouped together based on the absence of introns in the cloned genes, a common G-coupled protein transduction system (inhibition of adenylate cyclase), and similar operational characteristics. The 5-HT$_1$ family of inhibitory receptors includes subtypes A, B, D, E, and F. The 5-HT$_1$ G protein-linked receptors general inhibit the production of cyclic adenosine monophosphate (cAMP), while the 5-HT$_2$ G protein linked receptors stimulate phosphoinosytol hydrolysis.

The 5-HT$_{1A}$ receptor was the first cloned human serotonin receptor. Activated 5-HT$_{1A}$ receptors expressed in HeLa cells inhibit forskolin-stimulated adenylate cyclase activity.

The 5-HT$_{1D}$ receptor was originally identified in bovine brain membrane by Heuring and Peroutka. R. E. Heuring and S. J. Peroutka, *Journal of Neuroscience*, 7:894–903 (1987). The 5-HT$_{1D}$ receptors are the most common 5-HT receptor subtype in the human brain and may be identical to the 5-HT$_1$-like receptor in the cranial vasculature. S. D. Silberstein, *Headache*, 34:408–417 (1994). Sumatriptan and the ergot alkaloids have high affinity for both the human 5-HT$_{1D}$ and the 5-HT$_{1B}$ receptors. Id.

The 5-HT$_{1D}$ subtype of receptor has low affinity for 5-carboxamidotryptamine (5CT) unlike the other 5-HT receptors, except for the 5-HT$_{1E}$ subtype. Unlike the 5-HT$_{1E}$ receptors, however, the 5-HT$_{1F}$ receptors do show affinity for sumatriptan.

TABLE I

| Receptor Type | Subtype | Location | Response |
|---|---|---|---|
| 5-HT$_1$ | 5-HT$_{1A}$ | Neuronal, mainly in CNS | Neuronal hyperpolarisation, hypotension |
| | 5-HT$_{1B}$ | CNS and some peripheral nerves | Inhibition of neurotransmitter release |
| | 5-HT$_{1D}$ | Mainly CNS | Inhibition of neurotransmitter release |
| | 5-HT$_{1E}$ | Only CNS | Inhibition of adenylyl cyclase |
| | 5-HT$_{1F}$ | Mainly CNS | Inhibition of adenylyl cyclase |
| | 5-HT$_1$-like | Intracranial vasculature | Smooth muscle contraction |
| 5-HT$_2$ | 5-HT$_{2A}$ | Vascular smooth muscle, platelets, lung, CNS, gastrointestinal tract | Vasoconstriction, platelet aggregation, bronchoconstriction |
| | 5-HT$_{2B}$ | Mainly peripheral, some CNS | Rat stomach fundic muscle contraction |
| | 5-HT$_{2C}$ | CNS (high density in choroid plexus) | upregulates phosphoinositide turnover |
| 5-HT$_3$ | | Peripheral and central neurones | Depolarization |
| 5-HT$_4$ | | Gastrointestinal tract, CNS, heart, urinary bladder | Activation of acetylcholine release in gut, tachycardia, upregulates cAMP in CNS neurones |
| 5-HT$_5$ | 5-HT$_{5A}$ | CNS | Not known |
| | 5-HT$_{5B}$ | CNS | Not known |
| 5-HT$_6$ | | CNS | Activation of adenylyl cyclase |
| 5-HT$_7$ | | CNS | Activation of adenylyl cyclase |

Serotonin Receptor Binding Activity
Binding to the 5-HT$_{1F}$ receptor.

The ability of a compound to bind to a serotonin receptor was measured using standard procedures. For example, the ability of a compound to bind to the 5-HT$_{1F}$ receptor subtype was performed essentially as described in N. Adham, et al., *Proceedings of the National Academy of Sciences (USA)*, 90:408–412 (1993).

The cloned 5-HT$_{1F}$ receptor was expressed in stably transfected LM(tk$^-$) cells. Membrane preparations were made by growing these transfected cell lines to confluency. The cells were washed twice with phosphate-buffered saline, scraped into 5 ml of ice-cold phosphate-buffered saline, and centrifuged at 200×g for about five minutes at 4° C. The pellet was resuspended in 2.5 ml of cold Tris buffer (20 mM Tris.HCl, pH 7.4 at 23° C., 5 mM EDTA) and homogenized. The lysate was centrifuged at 200×g for about five minutes at 4° C. to pellet large fragments. The supernatant was then centrifuged at 40,000×g for about 20 minutes at 4° C. The membranes were washed once in the homogenization buffer and resuspended in 25 mM glycylglycine buffer, pH 7.6 at 23° C.

Radioligand binding studies were performed using |$^3$H| 5-HT (20–30 Ci/mmol). Competition experiments were done by using various concentrations of drug and 4.5–5.5 nM |$^3$H|5-HT. Nonspecific binding was defined by 10 μM 5-HT. Binding data were analyzed by nonlinear-regression analysis. IC$_{50}$ values were converted to K$_i$ values using the Cheng-Prusoff equation.

For comparison purposes, the binding affinities of compounds for various serotonin receptors may be determined essentially as described above except that different cloned receptors are employed in place of the 5-HT$_{1F}$ receptor clone employed therein.

Serotonin Agonist Activity
Adenylate Cyclase Activity.

Adenylate cyclase activity was determined in initial experiments in LM(tk–) cells, using standard techniques. See, e.g., N. Adham, et al., supra,; R. L. Weinshank, et al., *Proceedings of the National Academy of Sciences (USA)*, 89:3630–3634 (1992), and the references cited therein.

Intracellular levels of cAMP were measured using the clonally derived cell line described above. Cells were pre-incubated for about 20 minutes at 37° C. in 5% carbon dioxide, in Dulbecco's modified Eagle's medium containing 10 mM HEPES, 5 mM theophylline, and 10 μM pargyline. Varying concentrations of the test compounds were added to the medium to determine inhibition of forskolin-stimulated adenylate cyclase.

Animal and human clinical models demonstrating the effectiveness of the methods of the present invention are well known to those skilled in the art. For example, the following experiment clearly demonstrates the inhibitory effect of the compounds of the present invention on an animal model predictive of migraine therapies.

Neurogenic Plasma Estravasation in the Dural Layer Induced by Electrical Stimulation Harlan Sprague-Dawley rats (225–325 g) or guinea pigs from Charles River Laboratories (225–325 g) were anesthetized with sodium phenobarbitol (65 mg/kg or 45 mg/kg, respectively, intraperitoneally) and placed in a stereotaxic frame (David Kopf Instruments) with the incisor bar set at –3.5 mm for rats or –4.0 mm for guinea pigs. Following a midline sagital scalp incision, two pairs of bilateral holes were drilled through the skull (6 mm posteriorly, 2.0 and 4.0 mm laterally for rats; 4 mm posteriorly and 3.2 and 5.2 mm laterally for guinea pigs—all coordinates reference to bregma). Pairs of stainless steel stimulating electrodes, insulated except for the tips, were lowered through the holes in both hemispheres to a depth of 9 mm (rats) or 10.5 mm (guinea pigs) from dura.

The femoral vein was exposed and a dose of the test compound was injected intravenously (1 ml/kg). Approximately seven minutes later, a 50 mg/kg dose of Evans Blue, a fluorescent dye, was also injected intravenously. The Evans Blue complexed with proteins in the blood and functioned as a marker for protein extravasation. Exactly ten minutes post-injection of the test compound, the left trigeminal ganglion was stimulated for three minutes at a current intensity of 1.0 mA (5 Hz, 4 msec duration) with a potentiostat/galvanostat.

Fifteen minutes following the stimulation, the animals were killed and exanguinated with 20 ml of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope equipped with a grating monochromator and a spectrophotometer was used to quantify the amount of Evans Blue dye in each tissue sample. An excitation wavelength of approximately 535 nm was utilized and the emission intensity at 600 nm was determined. The microscope was equipped with a motorized stage and was interfaced with a personal computer. This facilitated the computer-controlled movement of the stage with fluorescence measurements at 25 points (500 μm steps) on each dural sample. The mean and standard deviation of the measurements were determined by the computer.

The dural extravasation induced by electrical stimulation of the trigeminal ganglion was an ipsilateral effect (i.e. it occurs only on the side of the dura in which the trigeminal ganglion was stimulated). This allowed the other, unstimulated, half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was estimated.

Numerous recent publications have demonstrated that migraine and numerous psychiatric disorders are co-morbid. Individuals with migraine are at a higher risk of developing these disorders, which are described in detail infra. N. Breslau, et al., *Headache*, 34:387-393 (1994); K. R. Merikangas, et al., *Archives of General Psychiatry*, 47:849-853 (1990); N. Breslau, et al., *Psychiatry Research*, 37:11-23 (1991); W. F. Stewart, et al., *Psychosom. Medicine*, 51:559-569; J. Jarman, et al., *Journal of Neurological and Neurosurgical Psychiatry*, 53:573-575 (1990); V. Glover, et al., *Journal of Psychiatric Research*, 27:223-231 (1993); N. Breslau and G. C. Davis, *Journal of Psychiatric Research*, 27:211-221 (1993); and K. R. Merikangas, et al., *Journal of Psychiatric Research*, 27:197-210 (1993). This invention describes the co-morbidity of migraine pain and other pains such as those exemplified herein.

The methods of the present invention are particularly advantageous in the treatment or prevention of pain. These methods are especially preferred in the treatment or prevention of types of pain generally considered refractory to standard non-sedating, non-addictive therapies. Such pains include chronic pain, such as neuropathic pain, and postoperative pain, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

Animal and human clinical models demonstrating the effectiveness of the compounds of the present invention in treating psychiatric disorders are well known to those skilled in the art. For example, in evaluating the methods of the present invention in treating or preventing anxiety the following models may be employed.

Punished Responding

The antianxiety activity of the compositions employed in the method of the present invention is established by demonstrating that these compositions increase punished responding. This procedure has been used to establish antianxiety activity in clinically established compositions.

According to this procedure, the responding of rats or pigeons is maintained by a multiple schedule of food presentation. In one component of the schedule, responding produces food pellet presentation only. In a second component, responding produces both food pellet presentation and is also punished by presentation of a brief electric shock. Each component of the multiple schedule is approximately 4 minutes in duration, and the shock duration is approximately 0.3 seconds. The shock intensity is adjusted for each individual animal so that the rate of punished responding is approximately 15 to 30% of the rate in the unpunished component of the multiple schedule. Sessions are conducted each weekday and are approximately 60 minutes in duration. Vehicle or a dose of composition are administered 30 minutes to 6 hours before the start of the test session by the subcutaneous or oral route. Composition effects for each dose for each animal are calculated as a percent of the vehicle control data for that animal. The data are expressed as the mean ± the standard error of the mean.

Monkey Taming Model

The antianxiety activity of the compositions is established by demonstrating that the compositions are effective in the monkey taming model. Plotnikoff, *Res. Comm. Chem. Path. & Pharmacol.*, 5:128-134 (1973) describes the response of rhesus monkeys to pole prodding as a method of evaluating the antiaggressive activity of a test composition. In this method, the antiaggressive activity of a composition is considered to be indicative of its antianxiety activity. Hypoactivity and ataxia are considered to be indicative of a sedative component of the composition. The present study is designed to measure the pole prod response-inhibition induced by a composition of this invention in comparison with that of a standard antianxiety composition employing a compound such as diazepam as a measure of antiaggressive potential, and to obtain an indication of the duration of action of the compound.

Male and female rhesus or cynomologous monkeys, selected for their aggressiveness toward a pole, are housed individually in a primate colony room. Compositions or appropriate vehicle are administered orally or subcutaneously and the animals are observed by a trained observer at varying times after drug administration. A minimum of three days (usually a week or more) elapses between treatments. Treatments are assigned in random fashion except that no monkey receives the same composition two times consecutively.

Aggressiveness and motor impairment are graded by response to a pole being introduced into the cage as described in Table II. The individuals responsible for grading the responses are unaware of the dose levels received by the monkeys.

TABLE II

Grading of Monkey Response to Pole Introduction

| Response | Grade | Description |
|---|---|---|
| Attack | 2 | Monkey immediately grabbed and/or bit pole as it was placed at opening in cage. |
|  | 1 | Monkey grabbed and/or bit pole only after the tip was extended into the cage 12 inches or more. |
|  | 0 | No grabbing or biting observed. |
| Pole Push | 2 | Monkey grabbed the pole to attack it |

TABLE II-continued

Grading of Monkey Response to Pole Introduction

| Response | Grade | Description |
|---|---|---|
| | | or push it away. |
| | 1 | Monkey touched the pole only in attempting to avoid it or rode on the pole (avoidance). |
| | 0 | No pushing, grabbing or riding of the pole observed. |
| Biting | 2 | Monkey bit aggressively and frequently. |
| | 1 | Monkey bit weakly or infrequently |
| | 0 | No biting observed. |
| Ataxia | 2 | Monkey exhibited a marked loss of coordination. |
| | 1 | Slight loss of coordination observed. |
| | 0 | No effects on coordination observed. |
| Hypoactivity | 2 | Marked: Monkey was observed in a prone position. May or may not have responded by rising and moving away when experimenter approached. |
| | 1 | Slight: Monkey did not retreat as readily when experimenter approached |
| | 0 | None. |

Antiaggression Activity of Drug Dose

| | | |
|---|---|---|
| + | | Dose of drug was active in decreasing global assessment of aggressive behavior |
| − | | Dose of drug was not active in decreasing aggressive behavior |

Human Clinical Trials

Finally, the antianxiety activity of the named compositions and methdods can be demonstrated by human clinical trials. The study is designed as a double-blind, parallel, placebo-controlled multicenter trial. The patients are randomized into four groups, placebo and 25, 50, and 75 mg tid of test composition. The dosages are administered orally with food. Patients are observed at four visits to provide baseline measurements. Visits 5–33 served as the treatment phase for the study.

During the visits, patients and their caregivers were questioned and observed for signs of agitation, mood swings, vocal outbursts, suspiciousness, and fearfulness. Each of these behaviors are indicative of the effect of the test composition on an anxiety disorder.

The patient to be benefited by practice of the present invention is a patient having one or more of the disorders discussed in detail below, or who is at a heightened risk of contracting such disorder. Diagnosis of these disorders, or the identification of a patient at risk of one or more of them, is to be made by a physician or psychiatrist. It is presently believed that the combination of serotonin receptor agonists and tachykinin receptor antagonists results in the alleviation of the effects of the disorder from which the patient suffers, or even the elimination of the disorder completely.

A patient with a heightened risk of contracting one of the present disorders is a patient, in the present contemplation, who is more likely than is a normal person to fall victim to that disorder. The patient may have suffered from the disorder in the past, and be at risk of a relapse, or may exhibit symptoms which demonstrate to the physician or psychiatrist that the patient is under an abnormal risk of developing the disorder in its full form.

The disorders which are treated or prevented in the practice of the present invention may be described as follows.

bulimia nervosa
obsessive-compulsive disorder
premenstrual dysphoric disorder
substance abuse
substance dependence
panic disorder
panic attack
agoraphobia
post-traumatic stress disorder
dementia of Alzheimer's type
social phobia
attention deficit hyperactivity disorder
disruptive behavior disorder
intermittent explosive disorder
borderline personality disorder
chronic fatigue syndrome
premature ejaculation
depression and behavioral problems associated with head injury, mental retardation or stroke.

Most of the disorders discussed here are described and categorized in the DIAGNOSTIC AND STATISTICAL MANUAL OF MENTAL DISORDERS, (4th edition, 1994), published by the American Psychiatric Association (hereinafter referred to as DSM). In the discussion below, the DSM codes for the disorders will be given where appropriate.

Bulimia nervosa, DSM 307.51, is characterized by uncontrollable binge eating, followed by self-induced purging, usually vomiting. Its prevalence is as high as 1%–3% among adolescent and young adult females. The disorder is well characterized and recognized by the health professions. The essential features of it are binge eating and inappropriate compensatory methods to prevent weight gain. Further, individuals with the disorder are excessively influenced by body shape and weight.

Obsessive-compulsive disorder, DSM 300.3, is characterized by recurrent obsessions or compulsions which are severe enough to be time consuming or cause distress or impairment of the patient's life. Obsessions are persistent ideas, thoughts, impulses or images which are recognized by the patient to be intrusive and inappropriate and cause anxiety or distress. The individual senses that the obsession is alien, not under control and not the kind of thought that the patient would expect to have. Common obsessions include repeated thoughts about contamination, repeated doubts, a need to arrange things in a particular order, aggressive or horrific impulses and sexual imagery. Compulsions are repetitive behaviors, such as hand washing, or mental acts, such as counting or repeating words silently, the goal of which is to prevent or reduce anxiety or distress. By definition, compulsions are either clearly excessive or not realistically connected with that which they are designed to neutralize or prevent. Obsessive-compulsive disorder is rather common, with an estimated lifetime prevalence of 2.5%.

Substance abuse and substance dependence, very well known in most societies at present, come about when the patient becomes addicted or habituated to the improper use of a drug or other substance. Several different varieties of substance abuse and dependence will be discussed in detail below. It will be understood that substance abuse or dependence often results in additional disorders, including intoxication, withdrawal symptoms, delirium, psychotic disorders, hallucinations, mood disorders, anxiety disorders, sexual dysfunctions, or sleep disorders. Recognized substance abuse and substance dependence disorders which are part of the present invention include the following:

amphetamine dependence, DSM 304.40
amphetamine abuse, DSM 305.70
cannabis dependence, DSM 304.30
cannabis abuse, DSM 305.20
cocaine dependence, DSM 304.20
cocaine abuse, DSM 305.60
hallucinogen dependence, DSM 304.50
hallucinogen abuse, DSM 305.30
inhalant dependence, DSM 304.60
inhalant abuse, DSM 305.90
nicotine dependence, DSM 305.10
opioid dependence, DSM 304.00
opioid abuse, DSM 305.50
phencyclidine dependence, DSM 304.90
phencyclidine abuse, DSM 305.90
sedative, hypnotic or anxiolytic dependence, DSM 304.10
sedative, hypnotic or anxiolytic abuse, DSM 305.40
polysubstance dependence, DSM 304.80

The prevalence and deleterious effects of substance dependence and substance abuse are almost too well known to discuss. The disorders are characterized, in general, by a compulsion to use the substance in question in order to obtain its effects, regardless of the ill-effects of the substance or the difficulty, expense or danger of obtaining it. Some substances of abuse, such as cannabis and cocaine, have run through entire sections of society and have damaged or ruined untold numbers of lives. The importance of the ability to relieve such disorders in accordance with the present invention is obviously of great significance.

Panic attack, panic disorder and agoraphobia, categorized as DSM 300.01, 300.21 and 300.22, affect between 1.5% and 3.5% of the population. The disorders are characterized by irrational sense of imminent danger or doom, an urge to escape, or a fear of being in a situation from which escape might be difficult. The patient exhibits symptoms such as palpitations, accelerated heart rate, sweating, sensations of shortness of breath, chest pain, nausea, dizziness, fear of dying, and the like, and may have such attacks very frequently.

Social phobia, DSM 300.23, produces a marked and persistent fear of social or performance situations in which embarrassment may occur. Exposure to such a situation may result in a panic attack, or other anxious response. Most often, patients with the disorder simply avoid situations of the type which they dread, producing an obvious dislocation in the patient's life. The prevalence of social phobia has been reported as from 3% to 13%, on a lifetime basis.

Post-traumatic stress disorder, DSM 309.81, afflicts patients following exposure to a traumatic stress involving personal experience of an event involving actual or threatened death of injury. Such traumatic events include experiences such as military combat, personal assault, kidnapping, terrorist attack, torture, natural or man-made disasters, severe accidents, or being diagnosed with a dreaded illness. Learning about such events occurring to others, particularly a family member or close friend, also may produce the disorder. Triggering events which symbolize the traumatic event, such as an anniversary, may recreate the stress and bring on the disorder long after the event is passed. Patients strive to avoid stimuli associated with the trauma, even to the point of amnesia or reduced responsiveness to other people in general. Prevalence of post-traumatic stress disorder has been reported at from 1% to as much as 14%, and has been reported at 50% and more in studies of individuals who are at risk of the disorder.

Dementia of the Alzheimer's type, DSM 290.11, 290.12, 290.13, 290.10, 290.3, 290.20, 290.21 and 290.0, affects between 2% and 4% of the population over 65 years old. The prevalence increases with age, particularly after 75 years of age, and is associated with Alzheimer's disease. In most patients, brain atrophy or deterioration is present, and is associated with the dementia.

Attention deficit hyperactivity disorder, DSM 314.01 and 314.00, is primarily recognized as a disorder of children, but may well be found in adults as well. It is characterized by symptoms such as lack of attention, impulsivity, and excessive activity, resulting in high expenditure of effort accompanied with a low degree of accomplishment. Patients have difficulty or find it impossible to give attention to details, cannot sustain attention in tasks or even play, and make careless mistakes. They fail to listen to or follow through on instructions, lose things, and are easily distracted by extraneous events. The difficulty of such patients in carrying out useful lives is obvious from the mere recital of the symptoms.

Disruptive behavior disorder, DSM 312.9, is a condition characterized by aggressive, destructive, deceitful and defiant activity.

Intermittent explosive disorder, DSM 312.34, is characterized by episodes of failure to resist aggressive impulses, resulting in assault or destruction of property. The degree of aggressiveness expressed during episodes of this disorder is grossly disproportionate to any provocation or triggering stress. The Southeastern Asian condition of amok is an episode of this disorder, cases of which have been reported in Canada and the United States as well.

Borderline personality disorder, DSM 301.83, is marked by a pervasive pattern of instability of interpersonal relationships and self-image, and marked impulsivity which begins by early adulthood. Patients have a pattern of unstable and intense relationships, very quickly developing a very close relationship and then quickly devaluing the other person. Patients may gamble, spend irresponsibly, binge eat, abuse substances, engage in unsafe sex or drive recklessly. Patients often display recurrent suicidal behavior or self-injurious behavior. The prevalence is estimated to be about 2% of the population.

Premature ejaculation, DSM 302.75, is characterized by the inability of a male to delay orgasm as long as is desired.

Depression and behavioral problems associated with head injury, mental retardation or stroke are treated in the exercise of the present invention. Such depression and behavioral problems are distinct from the usual such disorders, because of their origin. Depression, of course, of the general type is quite prevalent and is now well-known, being well treated with pharmaceuticals such as, for example, fluoxetine.

Chronic fatigue syndrome is a condition which has been variously described and diagnosed. It is sometimes categorized as a low-grade viral infection, particularly caused by the Epstein-Barr virus. Since that virus is very widely found in the population, however, the diagnosis is problematic. An alternative characterization of chronic fatigue syndrome is a physical-psychological disorder of the depression type, characterized primarily by lack of energy and listlessness.

Premenstrual dysphoric disorder is characterized by symptoms such as feelings of sadness, hopelessness or self-deprecation; anxiety or tenseness; tearfulness and lability of mood; persistent irritability and anger; decreased interest in usual activities or withdrawal from relationships; difficulty concentrating and the like. It is not classified formally by DSM but is discussed in detail there. The pattern of symptoms occurs in most cycles, frequently beginning the week prior to menses. Frequently, the disorder markedly interferes with the patient's life in all respects during the attack of the disorder. The prevalence of the disorder in its most profound form has been estimated at 3%–5%, but there has been little systematic study on the course and stability of the condition.

Animal and human clinical models demonstrating the effectiveness of the compounds of the present invention in treating the common cold or allergic rhinitis are well known to those skilled in the art. For example, in evaluating the methods of the present invention in treating or ameliorating the symptoms of the common cold or allergic rhinitis, it is especially preferred to ultimately employ clinical studies. Human clinical studies for evaluating the effectiveness of a treatment of either of these disorders are described in U.S. Pat. Nos. 5,240,694, issued Aug. 31, 1993, and 5,252,602, issued Oct. 12, 1993, the entirety of which are herein incorporated by reference.

The compounds of Formula I have demonstrated efficacy as both tachykinin receptor antagonists and as serotonin agonists. As noted supra, U.S. patent application Ser. No.08/318,391, filed Oct. 5, 1994, describes a synergistic effect on the combination of a serotonin agonist and a tachykinin receptor antagonist in treating migraine. U.S. patent application Ser. No. 08/387,056, filed Feb. 10, 1995, describes a synergistic effect on the combination of a serotonin agonist and a tachykinin receptor antagonist in treating a variety of psychiatric disorders. U.S. patent application Ser. No. 08/408,238, filed Mar. 22, 1995, describes a synergistic effect on the combination of a serotonin agonist and a tachykinin receptor antagonist in treating a variety of types of pain and nociception. U.S. patent application Ser. No. 60/000,074, filed Jun. 8, 1995, describes a synergistic effect on the combination of a serotonin agonist and a tachykinin receptor antagonist in treating the common cold or allergic rhinitis.

The compounds of the present invention are, therefore, especially preferred for the treatment of these disorders. The most preferred methods of treatment of the present invention are those methods for which a synergistic effect can be demonstrated for compositions having activity as both tachykinin receptor antagonists and serotonin agonists.

The advantages of any synergistic combination therapy are obvious. Among its other advantages, this combination therapy greatly increases the therapeutic index of a composition in treating these nociceptive disorders. A markedly decreased amount of a serotonin agonist may now be administered to a patient, presumably greatly lessening the likelihood and severity of any adverse events. The reduced amount of active ingredient necessary for a therapeutic effect makes possible other routes of formulation than those currently employed. Rapid onset formulations such as buccal or sublingual may now be developed. Sustained release formulations are now more feasible due to the lower amounts of active ingredient necessary.

While it is possible to administer a compound employed in the methods of this invention directly without any formulation, the compounds are usually administered in the form of pharmaceutical compositions comprising a pharmaceutically acceptable excipient and at least one active ingredient. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

47

Formulation Example 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly.

Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of the formula wherein:

$R^1$, $R^2$, and $R^3$ are independently hydrogen, halo, $C_1$–$C_6$ alkoxy, $C_1$–$C_6$ alkylthio, nitro, trifluoromethyl, or $C_1$–$C_6$ alkyl;

A is —$CH_2$—, —$CH_2CH_2$—, or —$CH_2CH_2CH_2$—;

$R^a$ is hydrogen or hydroxy, and $R^b$ is hydrogen, or $R^a$ and $R^b$ are taken together to form a bond;

$R^4$ and $R^5$ are independently taken from the group consisting of halo, trifluoromethyl, hydrogen, $C_1$–$C_6$ alkoxy, $C_1$–$C_6$ alkyl, $C_1$–$C_6$ alkylthio, $C_1$–$C_6$ alkylamino, hydroxy, cyano, $C_2$–$C_7$ alkanoyl, $C_2$–$C_7$ alkanoyloxy, benzamido, phenoxy, carboxamido, hydroxy, benzyloxy, phenyl($C_2$–$C_7$ alkanoyl)-, phenyl ($C_2$–$C_7$ carbamoyl)-, said benzamido, phenoxy, benzyloxy, phenyl($C_2$-$C_7$ alkanoyl)-, and phenyl($C_2$-$C_7$ carbamoyl)-being optionally substituted with one or more groups selected from the group consisting of halo, trifluoromethyl, $C_1$-$C_6$ alkyl, $C_1$-$C_6$ alkoxy, cyano, hydroxy, amino and nitro;

or a pharmaceutically acceptable salt or solvate thereof.

2. A pharmaceutical formulation, comprising a compound of the formula

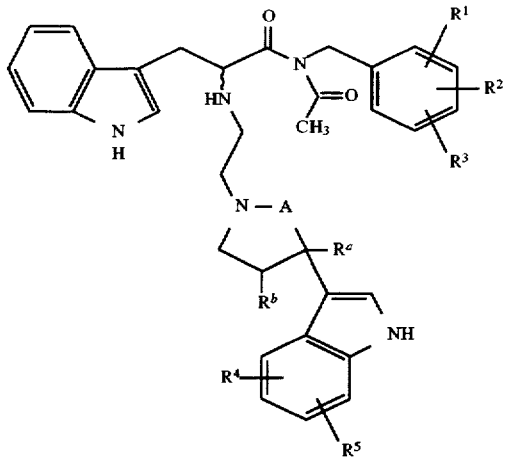

wherein:

$R^1$, $R^2$, and $R^3$ are independently hydrogen, halo, $C_1$-$C_6$ alkoxy, $C_1$-$C_6$ alkylthio, nitro, trifluoromethyl, or $C_1$-$C_6$ alkyl;

A is —CH2—, —$CH_2CH_2$—, or —$CH_2CH_2CH_2$—;

$R^a$ is hydrogen or hydroxy, and $R^b$ is hydrogen, or $R^a$ and $R^b$ are taken together to form a bond;

$R^4$ and $R^5$ are independently taken from the group consisting of halo, trifluoromethyl, hydrogen, $C_1$-$C_6$ alkoxy, $C_1$-$C_6$ alkyl, $C_1$-$C_6$ alkylthio, $C_1$-$C_6$ alkylamino, hydroxy, cyano, $C_2$-$C_7$ alkanoyl, $C_2$-$C_7$ alkanoyloxy, benzamido, phenoxy, carboxamido, hydroxy, benzyloxy, phenyl($C_2$-$C_7$ alkanoyl)-, phenyl ($C_2$-$C_7$ carbamoyl)-, said benzamido, phenoxy, benzyloxy, phenyl($C_2$-$C_7$ alkanoyl)-, and phenyl($C_2$-$C_7$ carbamoyl)-being optionally substituted with one or more groups selected from the group consisting of halo, trifluoromethyl, $C_1$-$C_6$ alkyl, $C_1$-$C_6$ alkoxy, cyano, hydroxy, amino and nitro;

or a pharmaceutically acceptable salt or solvate thereof, in combination with one or more pharmaceutically acceptable carriers, diluents, or excipients therefor.

* * * * *